US007513872B2

(12) United States Patent
Baba et al.

(10) Patent No.: US 7,513,872 B2
(45) Date of Patent: Apr. 7, 2009

(54) ULTRASONIC DOPPLER MEASURING APPARATUS AND CONTROL METHOD THEREFOR

(75) Inventors: Tatsuro Baba, Otawara (JP); Masami Takahashi, Nasushiobara (JP); Masao Takimoto, Otawara (JP); Muneki Kataguchi, Nasushiobara (JP); Takuya Sasaki, Nasu-gun (JP); Yasuo Miyajima, Utsunomiya (JP); Takanobu Uchibori, Otawara (JP); Tomio Nabatame, Nasu-gun (JP); Toshiyuki Koinuma, Shimotsuga-gun (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 362 days.

(21) Appl. No.: 11/250,440

(22) Filed: Oct. 17, 2005

(65) Prior Publication Data

US 2006/0084873 A1    Apr. 20, 2006

(30) Foreign Application Priority Data

Oct. 18, 2004    (JP)    ............................. 2004-303440

(51) Int. Cl.
*A61B 8/00*    (2006.01)
(52) U.S. Cl. .................................................... 600/455
(58) Field of Classification Search ................ 600/455, 600/457, 437, 454; 702/66, 189
See application file for complete search history.

(56) References Cited

U.S. PATENT DOCUMENTS 5,485,844 A    1/1996    Uchibori 6,050,948 A    4/2000    Sasaki et al.
6,306,093 B1*    10/2001    Wang ......................... 600/454
6,528,321 B1    3/2003    Fitzgerald et al.
2005/0080329 A1*    4/2005    Uchibori ..................... 600/407
2006/0084873 A1    4/2006    Baba et al.

FOREIGN PATENT DOCUMENTS

JP    7-303641    11/1995

OTHER PUBLICATIONS

U.S. Appl. No. 11/852,801, filed Sep. 10, 2007, Sasaki.
U.S. Appl. No. 11/084,159, filed Mar. 21, 2005, Masao Takimoto et al.
U.S. Appl. No. 12/140,607, filed Jun. 17, 2008, Baba et al.

* cited by examiner

*Primary Examiner*—Eric F Winakur
*Assistant Examiner*—Katherine L Fernandez
(74) *Attorney, Agent, or Firm*—Oblon, Spivak, McClelland, Maier & Neustadt, P.C.

(57) ABSTRACT

A Doppler sensitivity measuring unit measures the Doppler sensitivity of Doppler spectrum data obtained by ultrasonic wave transmission/reception with respect to a predetermined region of an object to be examined. A spectrum shape model generating unit generates a spectrum shape model on the basis of a window function used when the above Doppler spectrum data is generated. A threshold setting unit sets a threshold range in which trace waveform data displaces by a predetermined amount in the frequency axis direction on the basis of the spectrum shape model and the Doppler sensitivity, and sets a predetermined number of thresholds at almost equal intervals in the threshold range. A trace data generating unit selects a threshold for the acquisition of desired trace waveform data by generating trace waveform data while sequentially updating the plurality of set thresholds.

20 Claims, 13 Drawing Sheets

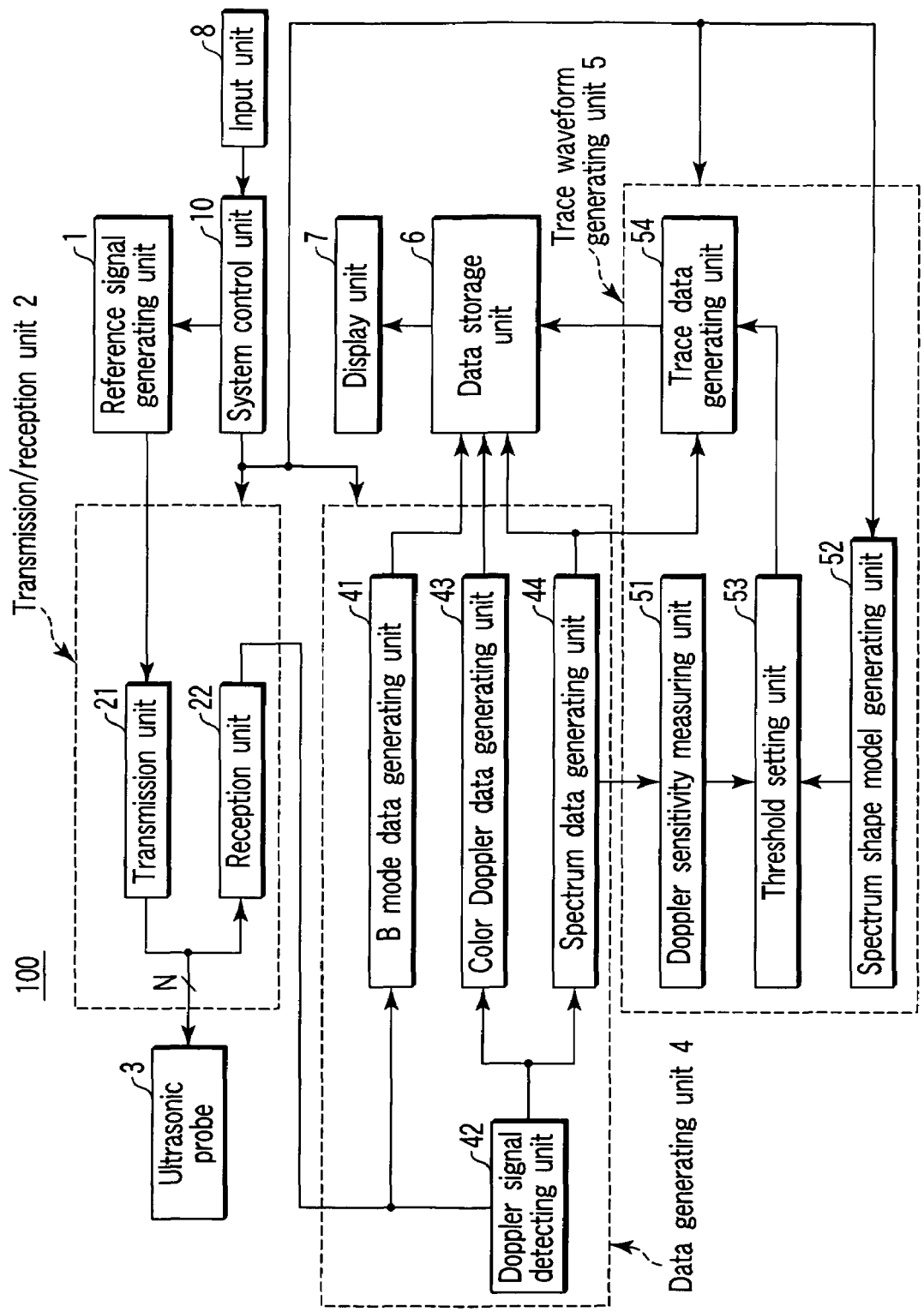
F I G. 2A

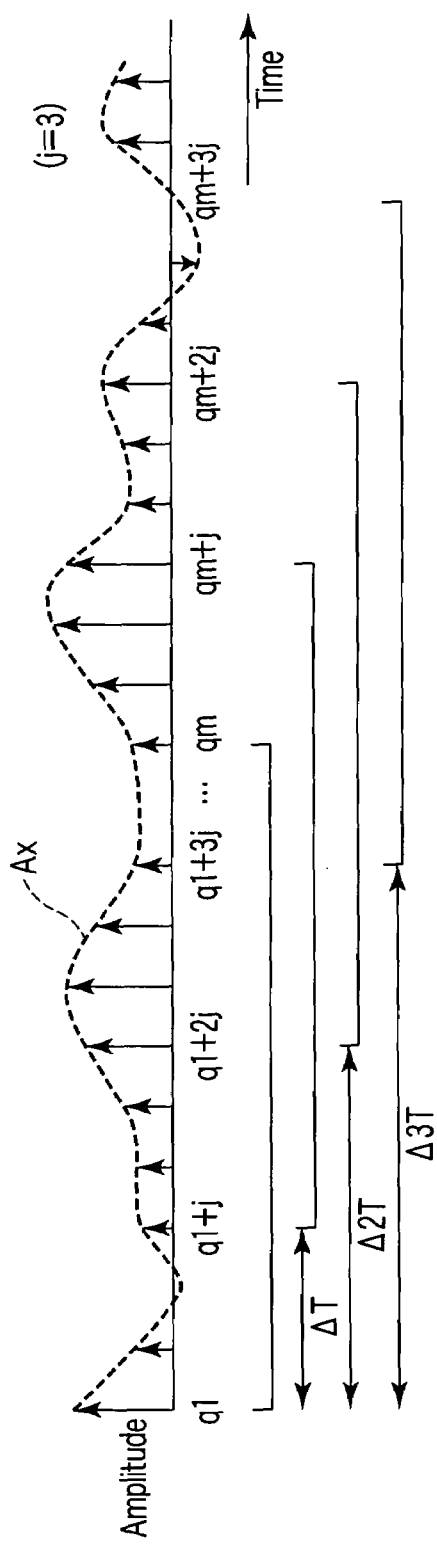
F I G. 4A
F I G. 4B
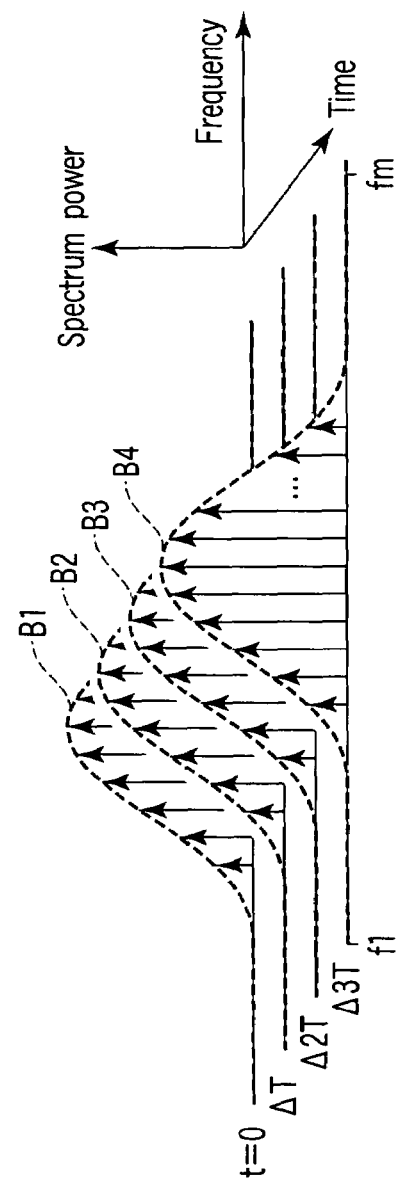
F I G. 4C

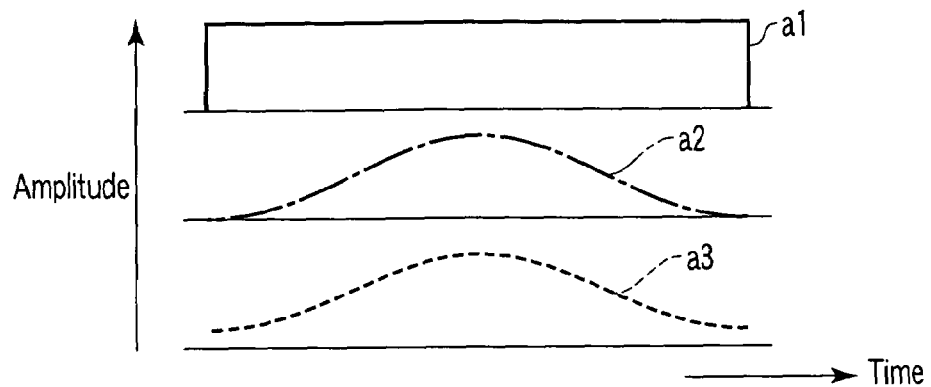
F I G. 6A
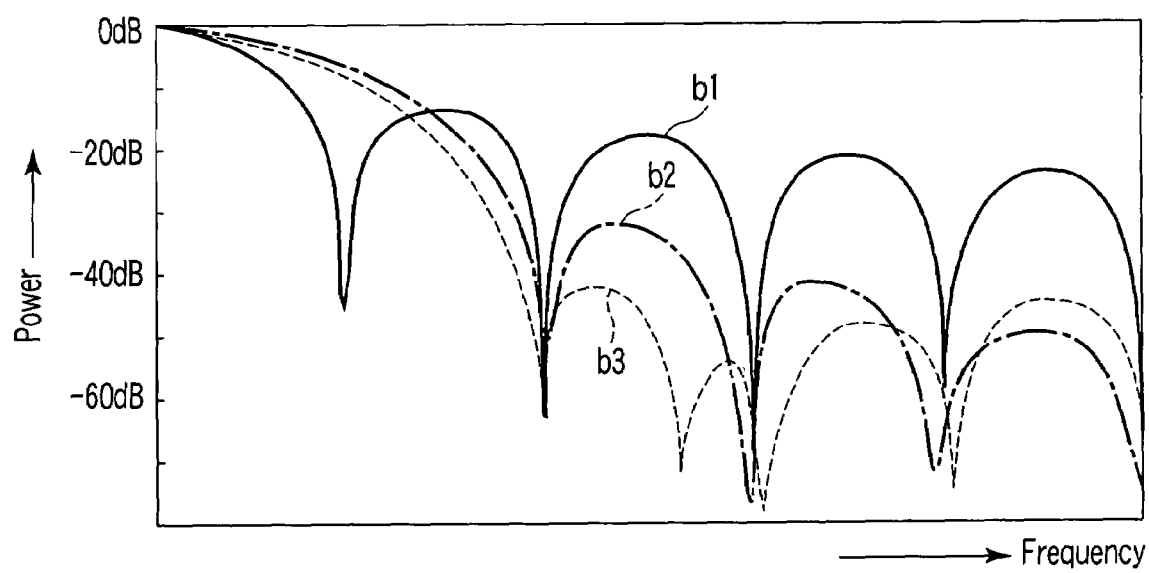
F I G. 6B

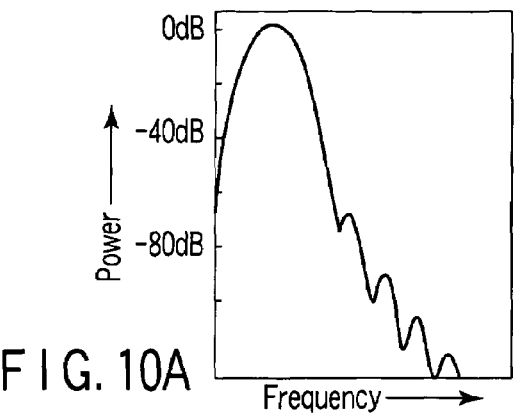
F I G. 10A
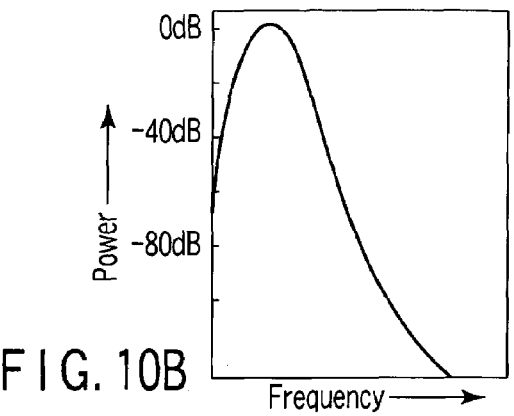
F I G. 10B
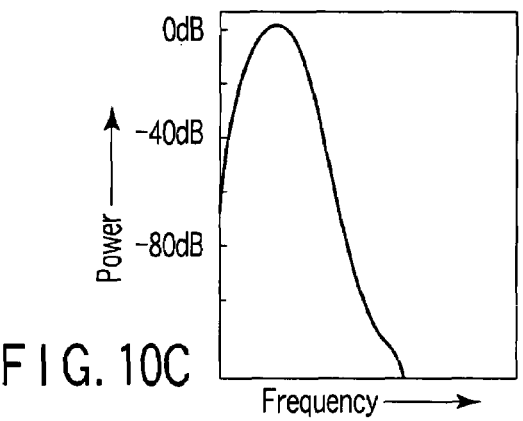
F I G. 10C
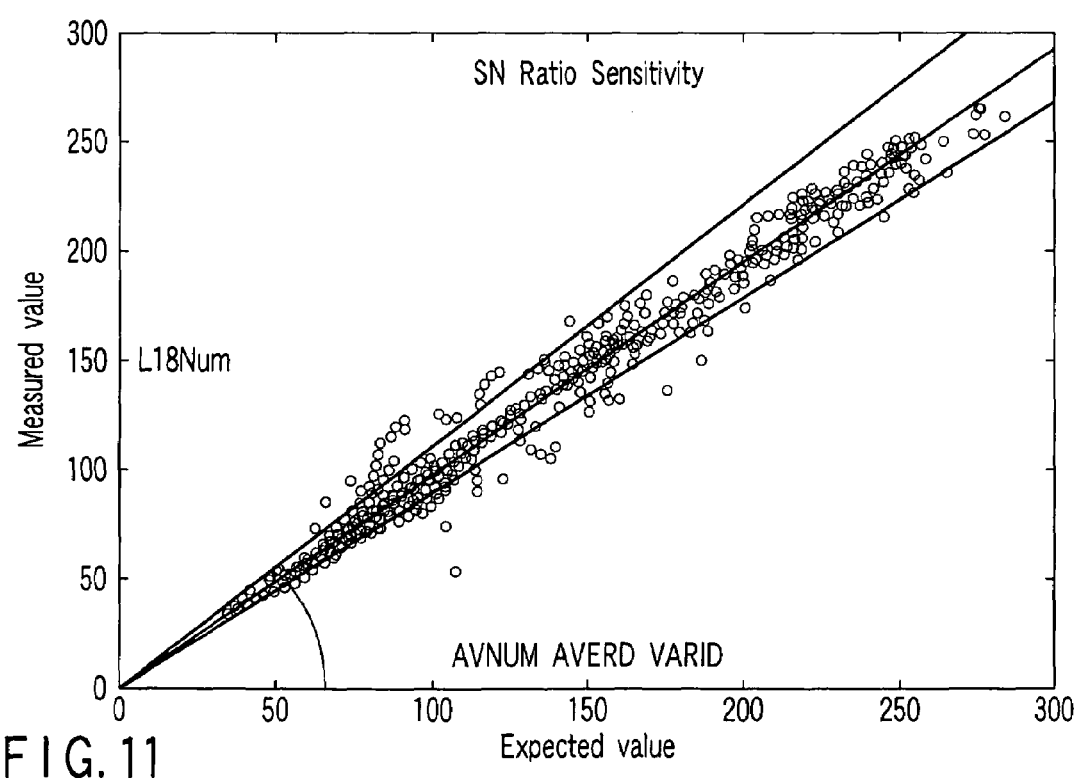
F I G. 11

ULTRASONIC DOPPLER MEASURING APPARATUS AND CONTROL METHOD THEREFOR

CROSS-REFERENCE TO RELATED APPLICATIONS

This application is based upon and claims the benefit of priority from prior Japanese Patent Application No. 2004-303440, filed Oct. 18, 2004, the entire contents of which are incorporated herein by reference.

BACKGROUND OF THE INVENTION

1. Field of the Invention

The present invention relates to an ultrasonic Doppler measuring apparatus which measures the flow velocity information of a blood flow and the movement information of tissue in a living body by using the Doppler effect of ultrasonic waves, and a control method therefor.

2. Description of the Related Art

An ultrasonic diagnostic apparatus is designed to apply ultrasonic pulses generated by ultrasonic transducers incorporated in an ultrasonic probe into an object to be examined, receive reflected ultrasonic waves generated by the difference in acoustic impedance between object tissues through the ultrasonic transducers, and display the resultant image on a monitor. This diagnostic method allows easy observation of a real-time two-dimensional image by simple operation of only bringing the ultrasonic probe into contact with the body surface, and hence is widely used for functional diagnosis or morphological diagnosis of various organs of a living body. Ultrasonic diagnostic methods of obtaining living body information by using reflected waves from tissue or blood cells in a living body have rapidly progressed along with two great technical developments of an ultrasonic pulse reflection method and ultrasonic Doppler method. B mode images and color Doppler images obtained by these techniques have become indispensable to recent ultrasonic image diagnosis.

A Doppler spectrum method is available as a method of obtaining blood flow information in an arbitrary observation region of an object quantitatively with high accuracy. In this Doppler spectrum method, ultrasonic wave transmission/reception is performed with respect to the same region of an object at predetermined intervals a plurality of number of times, and Doppler signals are detected by performing quadrature phase detection for reflected ultrasonic waves from moving reflectors such as blood cells by using a reference signal having a frequency almost equal to the resonance frequency of the ultrasonic transducers used for the reception of the ultrasonic waves. A Doppler signal in the desired region is extracted from these Doppler signals by using a range gate. Doppler spectrum data is generated by FFT-analyzing the extracted Doppler signal.

Doppler spectrum data are continuously generated with respect to the Doppler signal obtained from the desired region of the object according to such a sequence. The plurality of obtained Doppler spectrum data are sequentially arrayed to generate Doppler spectrum image data. Note that the range gate is set under B mode image observation to accurately set the range gate at the desired observation region in the object, and the position of the range gate is monitored with a B mode image.

The Doppler spectrum data obtained by this ultrasonic Doppler measuring apparatus is generally displayed with the ordinate representing a frequency (f), the abscissa representing time (t), and the power (intensity) of each frequency component being represented by a luminance (gray level). Various kinds of diagnosis parameters are measured on the basis of this Doppler spectrum data. As a typical method for this operation, there is available a method of detecting a maximum blood flow velocity Vp corresponding to a maximum frequency component fp in the frequency axis direction and measuring a diagnosis parameter on the basis of trace waveform data representing a temporal change in the maximum blood flow velocity Vp.

The trace waveform data of the maximum blood flow velocity Vp is generated by performing a method of measuring the maximum blood flow velocity Vp from the maximum value of Doppler spectrum components which are not buried in a noise spectrum. Conventionally, manual tracing operation has been basically performed with respect to frozen (freeze-displayed) Doppler spectrum data.

In contrast to this, recently, as disclosed in, for example, U.S. Pat. No. 6,528,321, a method of automatically tracing the maximum blood flow velocity Vp on the basis of a predetermined threshold set for Doppler spectrum data obtained in real time has been developed. In addition, there has been proposed a method of automatically setting the above threshold on the basis of the average signal level and average noise level of Doppler spectrum data. Furthermore, as disclosed in Jpn. Pat. Appln. KOKAI Publication No. 7-303641, there has also been proposed a method of setting a plurality of thresholds and selecting suitable trace waveform data as the trace waveform data of the maximum blood flow velocity Vp from a plurality of trace waveform data generated on the basis of the thresholds.

According to the method disclosed in U.S. Pat. No. 6,528,321 described above, in some case, however, the maximum blood flow velocity Vp cannot be detected as it is influenced by noise with temporal variations in average signal level and average noise level. For this reason, a doctor or examination technician (to be referred to as an operator hereinafter) needs always to execute a sequence of sequentially updating the above threshold and setting a threshold for the acquisition of desired trace waveform data by observing sequentially generated trace waveform data.

When trace waveform data are to be generated while a threshold for Doppler spectrum data is updated at predetermined intervals, the displacement amount of trace waveform data with respect to the amount of change in threshold depends on the average signal level and average noise level of Doppler spectrum data. If, for example, the difference between an average signal level and an average noise level (to be referred to as a Doppler sensitivity) is large as in the case with Doppler spectrum data obtained from a blood flow in the common carotid artery, a slight change in threshold has no great influence on trace waveform data. If, however, the Doppler sensitivity is poor as in the case with the Doppler spectrum data of the middle cerebral artery or vertebral artery, trace waveform data noticeably displaces in the frequency axis direction with the same amount of change in threshold. It is known that a Doppler sensitivity depends on the sex and constitutional predisposition (e.g., the degree of obesity) of an object as well as a measurement region. The same phenomenon as that described above occurs in trace waveform data obtained with respect to such an object.

FIG. 1A shows trace waveform data obtained when three thresholds are set at predetermined intervals with respect to Doppler spectrum data obtained from the common carotid artery with a good Doppler sensitivity. Referring to FIG. 1A, the ordinate represents the blood flow velocity (frequency); and the abscissa, the time. FIG. 1B shows trace waveform data obtained when three thresholds are set at the same intervals as those in FIG. 1A with respect to Doppler spectrum data obtained from the middle cerebral artery with a poor Doppler sensitivity. Referring to FIG. 1B, the ordinate and abscissa represent the same as those in FIG. 1A.

Therefore, in order to efficiently select a threshold for the generation of desired trace waveform data from a plurality of thresholds set in advance, it is preferable to compare and observe trace waveform data obtained while updating a threshold at relatively short intervals with respect to Doppler spectrum data exhibiting a poor Doppler sensitivity and updating a threshold at relatively long intervals with respect to Doppler spectrum data exhibiting a good Doppler sensitivity. However, there is no description about a method of setting threshold intervals accompanying differences in Doppler sensitivity in the method disclosed in U.S. Pat. No. 6,528, 321 or Jpn. Pat. Appln. KOKAI Publication No. 7-303641 described above.

BRIEF SUMMARY OF THE INVENTION

The present invention has been made in consideration of such problems in the prior art, and has as its object to provide an ultrasonic Doppler measuring apparatus in which when desired trace waveform data is to be generated by setting a threshold for time-serially obtained Doppler spectrum data, a threshold range is set with respect to the Doppler spectrum data on the basis of a spectrum shape model and Doppler sensitivity, and the desired trace waveform data can be efficiently and accurately generated by sequentially updating a predetermined number of thresholds set in the threshold range, and a control method for the apparatus.

In order to achieve the above object, the present invention uses the following techniques.

According to an aspect of the present invention, there is provided an ultrasonic Doppler measuring apparatus which comprises: an ultrasonic probe having an ultrasonic transducer which performs ultrasonic wave transmission/reception in a predetermined direction of an object to be examined; a transmission unit which transmits an ultrasonic wave by driving the ultrasonic transducer; a reception unit which receives a reception signal from the object which is obtained by transmission/reception of the ultrasonic wave; a Doppler signal detecting unit which detects a Doppler signal with respect to the reception signal; a spectrum data generating unit which time-serially generates Doppler spectrum data time-serially by repeating ultrasonic wave transmission/reception in the predetermined direction; a threshold setting unit which sets a threshold range to a predetermined parameter and sets a plurality of thresholds in the threshold range, the predetermined parameter being used to set a condition to generate waveform data from the Doppler spectrum data; a trace data generating unit which generates as the trace waveform data a temporal change in Doppler frequency of the spectrum data which corresponds to a threshold selected from said plurality of thresholds; and a display unit which displays the trace waveform data, wherein the threshold setting unit sets the threshold range and the plurality of thresholds on the basis of the Doppler spectrum data.

According to another aspect of the present invention, there is provided an ultrasonic Doppler measuring apparatus which comprises: an ultrasonic probe having an ultrasonic transducer which performs ultrasonic wave transmission/reception in a predetermined direction of an object to be examined; a transmission unit which transmits an ultrasonic wave by driving the ultrasonic transducer; a reception unit which receives a reception signal from the object which is obtained by transmission/reception of the ultrasonic wave; a Doppler signal detecting unit which detects a Doppler signal with respect to the reception signal; a spectrum data generating unit which time-serially generates Doppler spectrum data by setting a predetermined window function for the Doppler signals at a predetermined region which are time-serially obtained by repeating ultrasonic wave transmission/reception in the predetermined direction; a Doppler sensitivity measuring unit which measures a Doppler sensitivity on the basis of said plurality of Doppler spectrum data generated by the spectrum data generating unit; a spectrum shape model generating unit which generates a spectrum shape model on the basis of the window function; a threshold setting unit which sets a threshold range in which trace waveform data displaces by a predetermined amount in a frequency axis direction and sets a plurality of thresholds in the threshold range on the basis of the spectrum shape model and the Doppler sensitivity; a trace data generating unit which generates as the trace waveform data a temporal change in Doppler frequency of the Doppler spectrum data which corresponds to a threshold selected from said plurality of thresholds; and a display unit which displays the trace waveform data.

According to yet another aspect of the present invention, there is provided an ultrasonic Doppler measuring apparatus control method which comprises: transmitting an ultrasonic wave by driving an ultrasonic transducer which performs ultrasonic wave transmission/reception in a predetermined direction of an object to be examined; receiving a reception signal from the object which is obtained by transmission/ reception of the ultrasonic wave; detecting a Doppler signal from the reception signal; time-serially generating Doppler spectrum data by repeating ultrasonic wave transmission/ reception in the predetermined direction; setting a threshold range to a predetermined parameter and sets a plurality of thresholds in the threshold range, the predetermined parameter being used to set a condition to generate waveform data from the Doppler spectrum data; generating as the trace waveform data a temporal change in Doppler frequency of the spectrum data which corresponds to a threshold selected from said plurality of thresholds; and displaying the trace waveform data, wherein the threshold setting unit sets the threshold range and the plurality of thresholds on the basis of the Doppler spectrum data.

According to yet another aspect of the present invention, there is provided an ultrasonic Doppler measuring apparatus control method which comprises: transmitting an ultrasonic wave by driving an ultrasonic transducer which performs ultrasonic wave transmission/reception in a predetermined direction of an object to be examined; receiving a reception signal from the object which is obtained by transmission/ reception of the ultrasonic wave; detecting a Doppler signal from the reception signal; time-serially generating Doppler spectrum data by setting a predetermined window function for the Doppler signals at a predetermined region which are time-serially obtained by repeating ultrasonic wave transmission/reception in the predetermined direction; measuring a Doppler sensitivity on the basis of said plurality of generated Doppler spectrum data; generating a spectrum shape model on the basis of the window function; setting a threshold range in which trace waveform data displaces by a predetermined amount in a frequency axis direction and setting a plurality of thresholds in the threshold range on the basis of the spectrum shape model and the Doppler sensitivity; generating a temporal change in Doppler frequency of the spectrum data which corresponds to a threshold selected from said plurality of thresholds as the trace waveform data; and displaying the trace waveform data.

BRIEF DESCRIPTION OF THE SEVERAL VIEWS OF THE DRAWING

FIG. 2A is a block diagram showing the overall arrangement of an ultrasonic Doppler measuring apparatus according to the first embodiment of the present invention;

FIGS. 4A to 4C are views showing a method of generating Doppler spectrum data in the first embodiment;

FIGS. 6A and 6B are views showing specific examples of a window shape and spectrum shape model in the first embodiment;

FIGS. 10A to 10C are graphs each showing a modification of a spectrum shape model in the first embodiment;

FIG. 11 is a correlation diagram on which expected values on the frequency axis and measured values obtained by this apparatus are plotted in the respective time phases;

DETAILED DESCRIPTION OF THE INVENTION

Figure 1A:
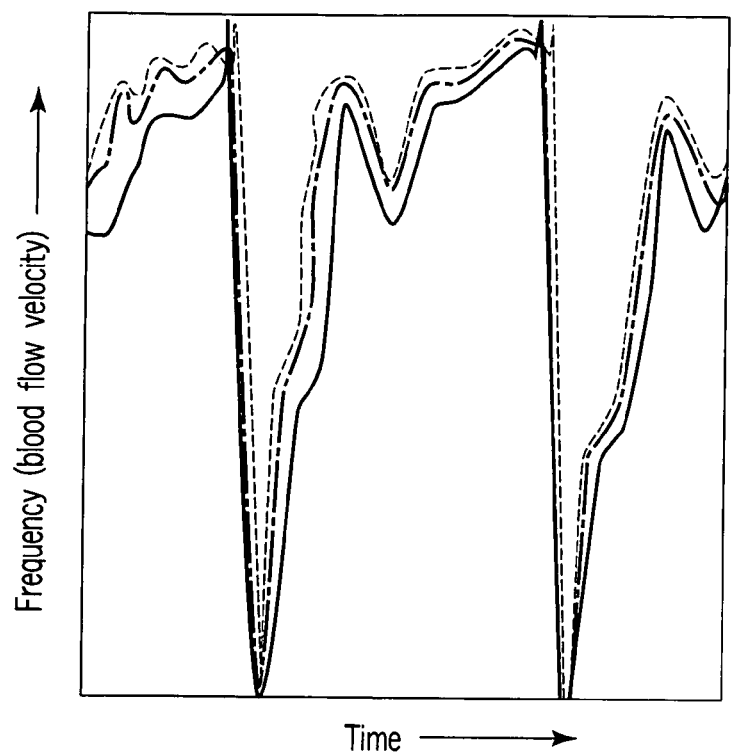
FIGS. 1A and 1B are graphs for explaining problems in the generation of trace waveform data in the prior art.
Figure 1B:
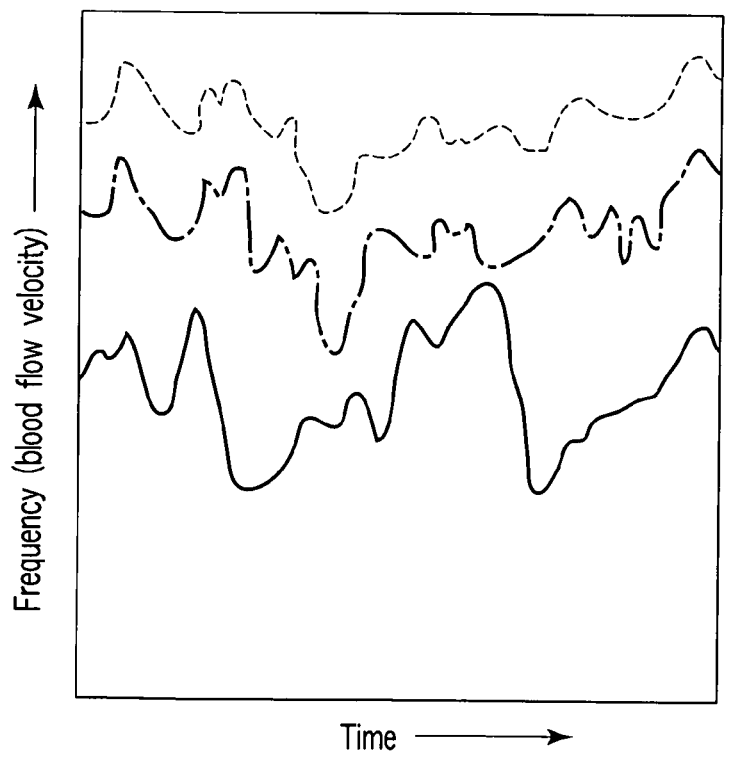

The first and second embodiments of the present invention will be described below with reference to the views of the accompanying drawing. Note that the same reference numerals in the following description denote constituent elements having substantially the same functions and arrangements, and a repetitive description will be made only when required.

FIRST EMBODIMENT (Arrangement of Apparatus)

In the following embodiment of the present invention, a Doppler sensitivity is measured from the average signal level and average noise level of Doppler spectrum data obtained by ultrasonic wave transmission/reception with respect to a predetermined region of an object to be examined. A threshold range in which trace waveform data changes by a predetermined amount in the frequency axis direction is set on the basis of a spectrum shape model generated on the basis of a window function for the generation of the above Doppler spectrum data and the above Doppler sensitivity, and a predetermined number of thresholds are set at almost equal intervals within the threshold range. A threshold by which desired trace waveform data can be obtained is selected from the plurality of set thresholds, and the generation and display of trace waveform data are continued by using the selected threshold.

Figure 2B:
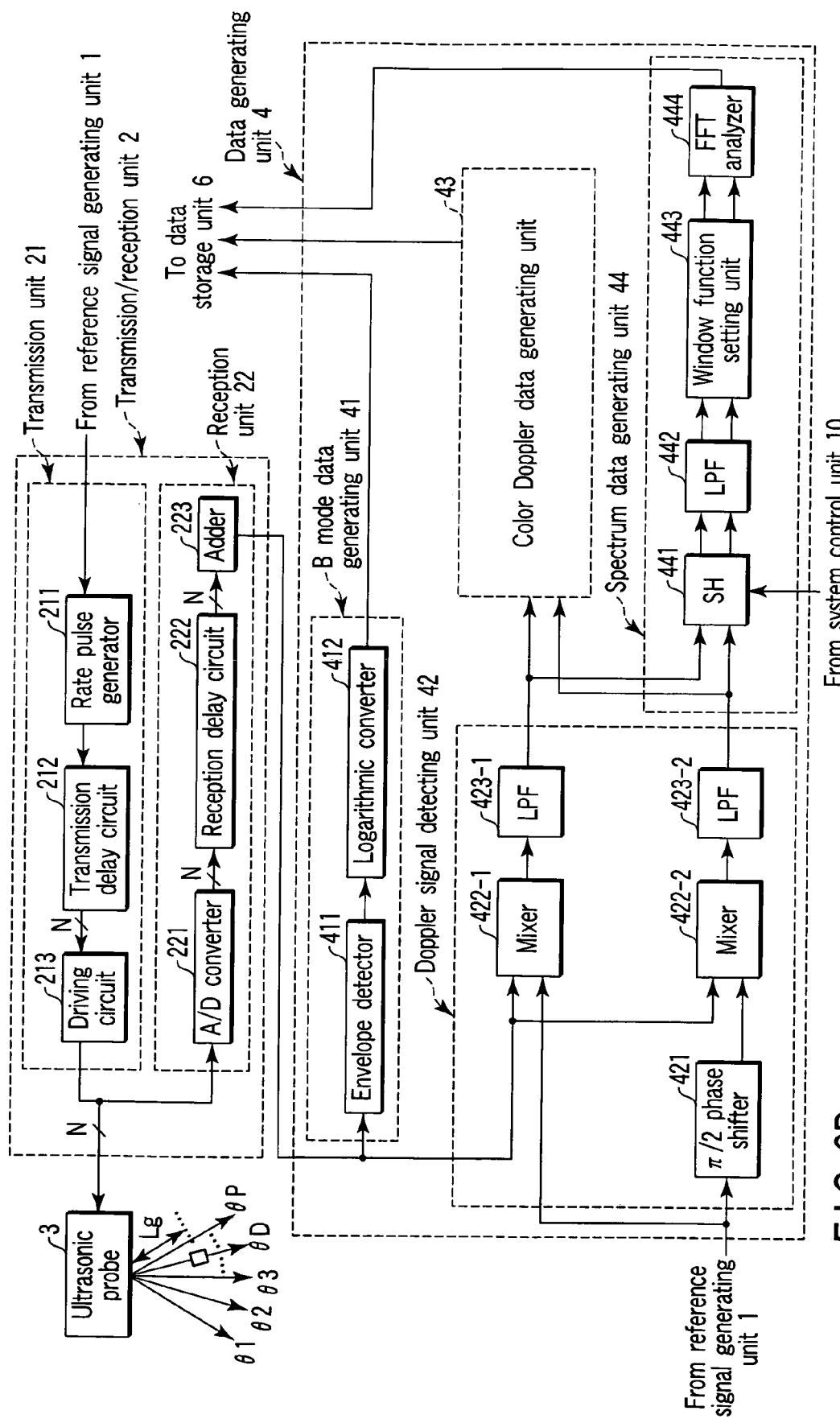
FIG. 2B is a block diagram showing the arrangements of a transmission/reception unit and data generating unit in the first embodiment.

The arrangement of an ultrasonic Doppler measuring apparatus and the basic operation of each unit in an embodiment of the present invention will be described below. FIG. 2A is a block diagram showing the overall arrangement of an ultrasonic Doppler measuring apparatus according to this embodiment. FIG. 2B is a block diagram of a transmission/reception unit and data generating unit which constitute this ultrasonic Doppler measuring apparatus.

An ultrasonic Doppler measuring apparatus 100 shown in FIG. 2A comprises an ultrasonic probe 3 which transmits/receives ultrasonic waves to/from an object to be examined, a transmission/reception unit 2 which performs transmission/reception with respect to the ultrasonic probe 3, and a data generating unit 4 which performs signal processing for obtaining B mode data, color Doppler data, and Doppler spectrum data from reception signals obtained from the transmission/reception unit 2. This apparatus further comprises a trace waveform generating unit 5 which generates the trace waveform data of a maximum blood flow velocity Vp on the basis of the Doppler spectrum data generated by the data generating unit 4 and a data storage unit 6 which generates and stores B mode image data, color Doppler image data, and Doppler spectrum image data from the above data time-serially obtained by the data generating unit 4, and stores the trace waveform data generated by the trace waveform generating unit 5.

Furthermore, the ultrasonic Doppler measuring apparatus 100 comprises a reference signal generating unit 1 which generates, for example, a continuous or rectangular wave having a frequency almost equal to the center frequency of ultrasonic pulses with respect to the transmission/reception unit 2 or data generating unit 4, a display unit 7 which displays, for example, image data or trace waveform data stored in the data storage unit 6, an input unit 8 which is used by an operator to, for example, input patient information, set an image display mode, set conditions for the generation of various kinds of image data and trace waveform data, and input various kinds of command signals, and a system control unit 10 which systematically controls the above respective units of the ultrasonic Doppler measuring apparatus 100.

The ultrasonic probe 3 transmits/receives ultrasonic waves to/from the surface of the object while the front surface of the probe is in contact with the surface, and has a one-dimensional array of a plurality of (N) minute ultrasonic transducers at the distal end portion of the probe. Each ultrasonic transducer is an electroacoustic conversion element, which has a function of converting an electrical pulse into an ultrasonic pulse (transmission ultrasonic wave) at the time of transmission and converting a reflected ultrasonic wave (reception ultrasonic wave) into an electrical signal (reception signal) at the time of reception. Each of the above plurality of ultrasonic transducers is connected to the transmission/reception unit 2 through a cable (not shown). The ultrasonic probe 3 includes probes for sector scanning, linear scanning, and convex scanning, one of which is arbitrarily selected in accordance with a diagnosis region. The following description will exemplify the ultrasonic probe 3 for sector scanning. However, the present invention is not limited to this, and this probe may be that for linear scanning or convex scanning.

The transmission/reception unit 2 shown in FIGS. 2A and 2B comprises a transmission unit 21 which generates a driving signal for making the ultrasonic probe 3 emit transmission ultrasonic waves and a reception unit 22 which performs phased addition of reception signals from the ultrasonic probe 3.

The transmission unit 21 comprises a rate pulse generator 211, transmission delay circuit 212, and driving circuit 213. The rate pulse generator 211 generates a rate pulse for determining the repetition period of transmission ultrasonic waves by frequency-dividing a continuous wave or rectangular wave supplied from the reference signal generating unit 1, and supplies the rate pulse to the transmission delay circuit 212.

The transmission delay circuit 212 is comprised of independent delay circuits equal in number to the ultrasonic transducers (N channels) used for transmission. The transmission delay circuit 212 gives a rate pulse a delay time for focusing a transmission ultrasonic wave to a predetermined depth so as to obtain a small beam width at the time of transmission and a delay time for applying a transmission ultrasonic wave in a predetermined direction, and supplies the resultant rate pulse to the driving circuit 213. The driving circuit 213 has independent driving circuits corresponding to N channels, and generates driving pulses for driving the ultrasonic transducers incorporated in the ultrasonic probe 3 on the basis of the rate pulse.

The reception unit 22 comprises an A/D converter 221, reception delay circuit 222, and adder 223 each comprising N channels. N-channel reception signals supplied from the ultrasonic probe 3 are converted into digital signals by the A/D converter 221 and sent to the reception delay circuit 222. The reception delay circuit 222 gives each of the N-channel reception signals output from the A/D converter 221 a focusing delay time for focusing a reflected ultrasonic wave from a predetermined depth and a deflection delay time for setting reception directivity with respect to a predetermined direction. The adder 223 then performs phased addition of reception signals from the reception delay circuit 222 (addition of reception signals obtained from a predetermined direction upon phase matching).

The data generating unit 4 comprises a B mode data generating unit 41 which generates B mode data with respect to the reception signal output from the adder 223 of the reception unit 22, a Doppler signal detecting unit 42 which detects a Doppler signal by performing quadrature detection of the reception signal, a color Doppler data generating unit 43 which generates color Doppler data on the basis of the detected Doppler signal, and a spectrum data generating unit 44 which generates spectrum data by frequency analysis of the Doppler signal.

The B mode data generating unit 41 comprises an envelope detector 411 and logarithmic converter 412. The envelope detector 411 performs envelope detection of the reception signal after phased addition which is supplied from the adder 223 of the reception unit 22. The amplitude of this envelope detection signal is logarithmically converted by the logarithmic converter 412. Note that the arrangement order of the envelope detector 411 and logarithmic converter 412 may be reversed.

The Doppler signal detecting unit 42 comprises a n/2 phase shifter 421, mixers 422-1 and 422-2, and LPFs (Low-Pass Filters) 423-1 and 423-2, and detects a Doppler signal by performing quadrature phase detection for the reception signal supplied from the adder 223 of the reception unit 22 by the operation to be described later.

The color Doppler data generating unit 43 comprises a Doppler signal storage circuit 431, MTI filter 432, autocorrelation computing unit 433, and the like (which are not shown), and calculates the average flow velocity value and variance of a blood flow on the basis of the Doppler signal detected by the Doppler signal detecting unit 42. In this embodiment, however, this unit is not an essential constituent element, and hence a detailed description thereof will be omitted.

The spectrum data generating unit 44 comprises an SH (Sample/Hold circuit) 441, LPF (Low-Pass Filter) 442, window function setting unit 443, and an FFT (Fast-Fourier-Transform) analyzer 444, and performs FFT analysis for the Doppler signal obtained by the Doppler signal detecting unit 42. Note that the SH 441 and LPF 442 each are comprised of two channels, to each of which the complex components of the Doppler signal output from the Doppler signal detecting unit 42, i.e., a real component (I component) and imaginary component (Q component), are supplied.

Figure 3:
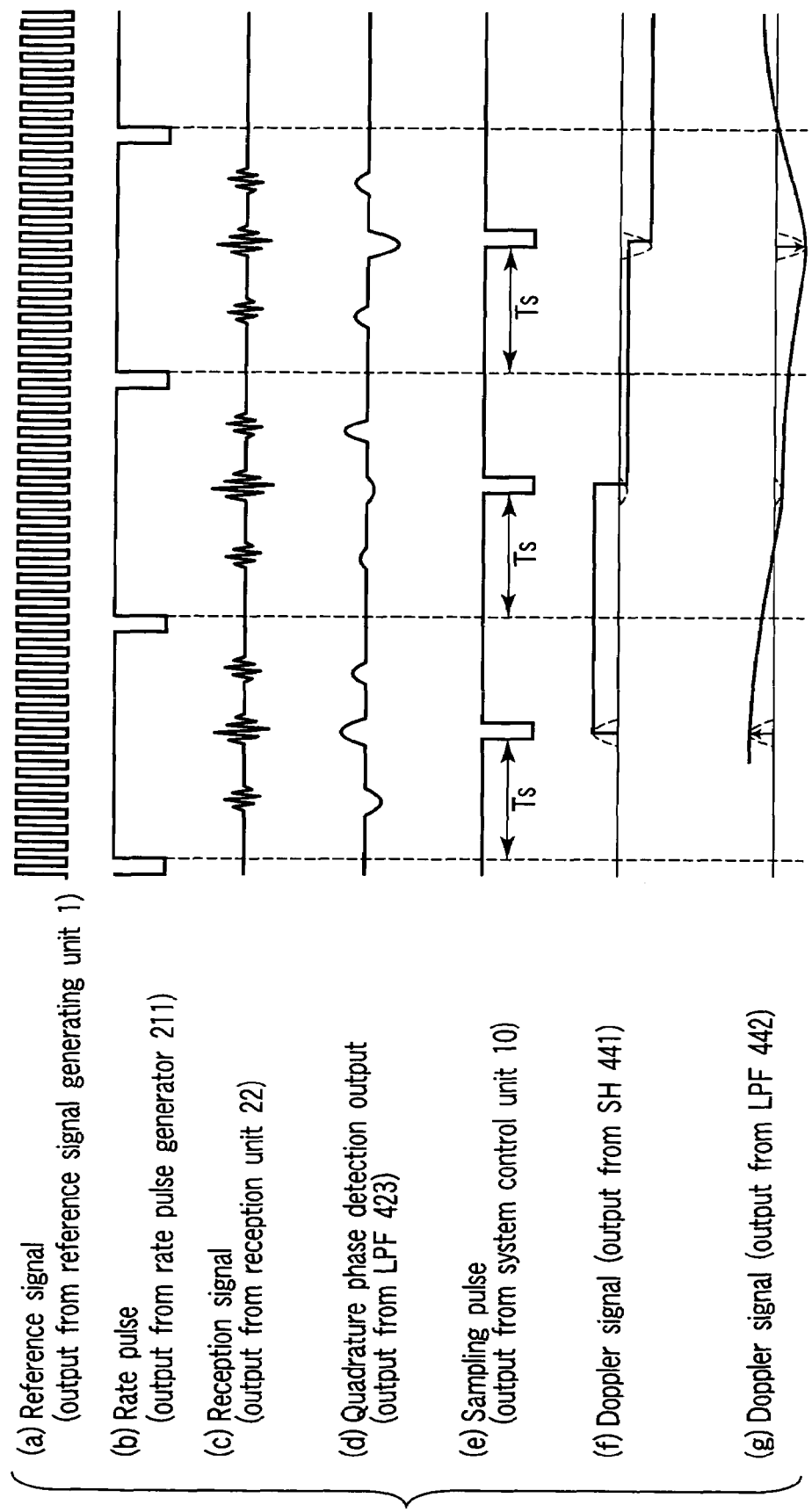
FIG. 3 is a timing chart showing the basic operations of a Doppler signal detecting unit and spectrum data generating unit in the first embodiment.

The basic operations of the Doppler signal detecting unit 42 and spectrum data generating unit 44 which are important constituent elements for the generation of Doppler spectrum data in the present invention will be described in detail next with reference to the timing chart of FIG. 3. For the sake of easy explanation, FIG. 3 shows a case wherein a Doppler component is detected from an analog reception signal. In actual processing, however, such detection is performed with respect to a digital reception signal output from the reception unit 22.

Referring to FIG. 3, reference symbol (a) denotes a reference signal output from the reference signal generating unit 1; (b), a rate pulse for a Doppler spectrum which is output from the rate pulse generator 211 of the transmission/reception unit 2; (c), a reception signal after phased addition which is obtained from the adder 223 of the reception unit 22; (d), a quadrature phase detection output from the LPF 423 of the Doppler signal detecting unit 42; (e), a sampling pulse which is supplied from the system control unit 10 to set a sampling (range gate) position of the SH 441 in the spectrum data generating unit 44; (f), a Doppler signal sampled/held by the SH 441; and (g), a Doppler signal in a range gate smoothed by the LPF 442.

The reception signal ((c) in FIG. 3) output from the reception unit 22 in FIGS. 2A and 2B is input to the first input terminal of each of the mixers 422-1 and 422-2 of the Doppler signal detecting unit 42. On the other hand, the reference signal ((a) in FIG. 3) which is generated by the reference signal generating unit 1 and has a repetition frequency almost equal to the center frequency of this reception signal is directly supplied to the second input terminal of the mixer 422-1, and the reference signal obtained by 90° phase shift in the n/2 phase shifter 421 is sent to the second input terminal of the mixer 422-2. The outputs from the mixers 422-1 and 422-2 are sent to the LPFs 423-1 and 423-2, and the sum component of the frequency of the reception signal supplied from the reception unit 22 and the repetition frequency of the reference signal supplied from the reference signal generating unit 1 is removed from each other, and only the difference component is extracted as a Doppler signal ((d) in FIG. 3).

The Doppler signals output from the LPFs 423-1 and 423-2 and the sampling pulse (range gate pulse) generated by the system control unit 10 by frequency-dividing the reference signal from the reference signal generating unit 1 are supplied to the SH 441 of the spectrum data generating unit 44 ((e) in FIG. 3). A Doppler signal from a desired distance is sampled/held with this sampling pulse ((f) in FIG. 3). Note that this sampling pulse is generated a delay time Ts after the rate pulse ((b) in FIG. 3) for determining the timing of the emission of a transmission ultrasonic wave. The delay time Ts can be arbitrarily set by the input unit 8.

By changing the delay time Ts of the sampling pulse, a Doppler signal at a desired distance Lg can be extracted from the ultrasonic probe 3. Note that letting C be the sound velocity of an object, the delay time Ts and desired distance Lg have the relationship represented by $2Lg/C=Ts$.

The staircase noise component superimposed on the Doppler signal at the desired distance Lg output from the SH 441 is removed by the LPF 442 ((g) in FIG. 3), and the Doppler signal is smoothed. For the resultant Doppler signal, the window function setting unit 443 sets the data length of the Doppler signal in generating Doppler spectrum data, and performs predetermined weighting processing for the Doppler signal. The FFT analyzer 444 performs a fast Fourier transform of the Doppler signal for which weighting processing is performed by the window function setting unit 443, thereby generating Doppler spectrum data.

The window function setting unit 443 comprises a storage circuit in which coefficient data corresponding to rectangular, Hanning, and Hamming window shapes and the like are pre-stored and a computing circuit which multiplies the Doppler signal supplied from the LPF 442 by the above coefficient data. The computing circuit performs weighting processing based on the above window shape with respect to a Doppler signal in a predetermined interval which is extracted on the basis of the data length (observation time width) of a preset window function. The FFT analyzer 444 comprises a computing circuit and storage circuit (not shown), and temporarily stores, in the storage circuit, the Doppler signal after the weighting processing which is output from the window function setting unit 443. The computing circuit generates Doppler spectrum data by performing FFT analysis for the Doppler signal in the predetermined interval which is stored in this storage circuit.

FIGS. 4A to 4C show a method of generating Doppler spectrum data by using the window function setting unit 443 and FFT analyzer 444. FIG. 4A shows a Doppler signal Ax input to the window function setting unit 443. FIG. 4B shows a Hanning window shape for Doppler signal components $q_1$ to $q_m$ having a data length m set for the Doppler signal Ax.

FIG. 4C shows Doppler spectrum data B1, B2, B3, . . . obtained by performing FFT analysis for a Doppler signal for which a window function (i.e., a data length m and Hanning window shape) is set by the window function setting unit 443. That is, the first Doppler spectrum data B1 corresponding to spectrum components $f_1$ to $f_m$ is generated by performing weighting processing and FFT analysis for m Doppler signal components $q_1$ to $q_m$ of the discrete Doppler signal (FIG. 4A) supplied from the LPF 442 of the spectrum data generating unit 44. The first Doppler spectrum data B1 is generated for spectrum components $f_1$ to $f_m$. The new Doppler spectrum data B2 is then generated by performing weighting processing and FFT analysis for m Doppler signal components $q_{1+j}$ to $q_{m+j}$ after $\Delta T$.

Subsequently, likewise, the Doppler spectrum data B3, B4, . . . corresponding to the spectrum components $f_1$ to $f_m$ are generated by sequentially performing weighting processing and FFT analysis for m Doppler signal components $q_{1+2j}$ to $q_{m+2j}$ after $2\Delta T$, $q_{1+3j}$ to $q_{m+3j}$ after $3\Delta T$ (FIG. 4C), . . . . Note that FIG. 4A shows a case wherein j=3.

Referring back to FIG. 2A, the trace waveform generating unit 5 comprises a Doppler sensitivity measuring unit 51, spectrum shape model generating unit 52, threshold setting unit 53, and trace data generating unit 54.

The Doppler sensitivity measuring unit 51 comprises a computing circuit and storage circuit (not shown). The Doppler sensitivity measuring unit 51 measures a time-axis direction average value (average signal level) Sa (dB) of the maximum powers of a plurality of Doppler spectrum data time-serially supplied from the spectrum data generating unit 44 and a frequency-axis direction/time-axis direction average value (average noise level) Na (dB) of noise components, and further measures a Doppler sensitivity Ds (dB) from the difference between the average signal level Sa and the average noise level Na.

Figure 5A:
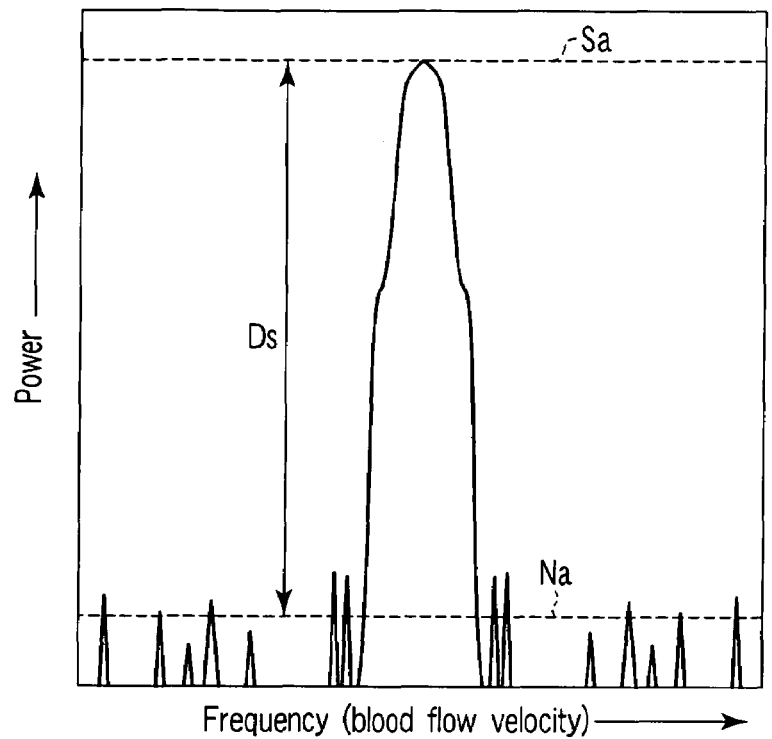
FIGS. 5A and 5B are graphs for explaining the average signal level, average noise level, and Doppler sensitivity of Doppler spectrum data in the first embodiment.
Figure 5B:
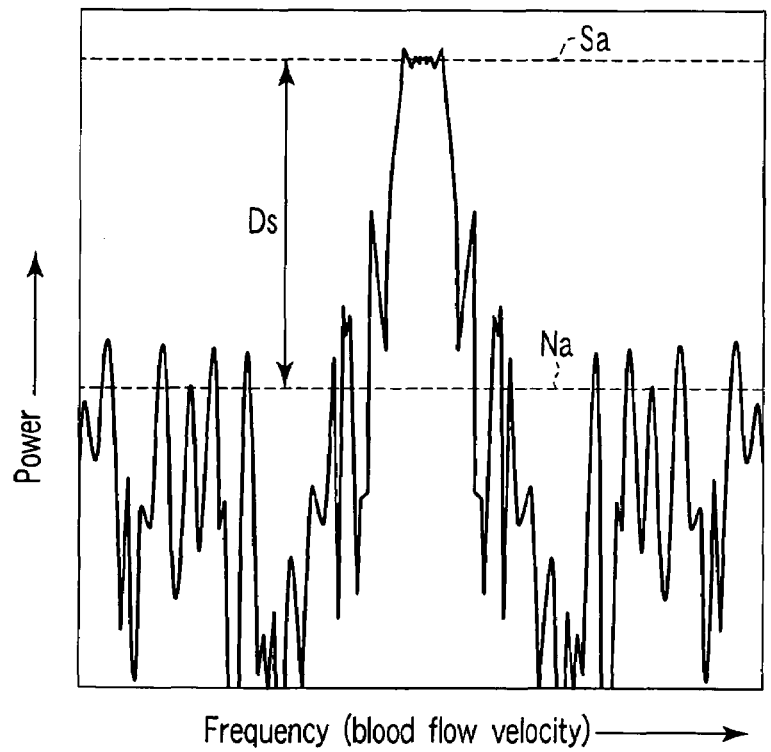

FIGS. 5A and 5B respectively show Doppler spectrum data (FIG. 5A) having a good Doppler sensitivity and Doppler spectrum data (FIG. 5B) having a poor Doppler sensitivity. The above Doppler spectrum data of the common carotid artery corresponds to the data shown in FIG. 5A, and the Doppler spectrum data of the middle cerebral artery corresponds to the data shown in FIG. 5B. Note that the ordinate and abscissa of these Doppler spectrum data respectively represent power and frequency (blood flow velocity). The Doppler sensitivity measuring unit 51 measures the average signal level Sa and average noise level Na of the respective Doppler spectrum data having different Doppler sensitivities and measures the Doppler sensitivity Ds.

The noise components of the Doppler spectrum data in FIG. 5A include a subsidiary maximum in the frequency axis direction which occurs when the window function initially set by the input unit 8 is Fourier-transformed, system noise of the apparatus which has small values relative to a Doppler signal, and reflected wave components other than those from blood cells. The noise components of the Doppler spectrum data in FIG. 5B include a subsidiary maximum equal in magnitude to that in FIG. 5A, system noise having a relatively large value, and reflected wave components other than those from blood cells.

The spectrum shape model generating unit 52 then receives the window function information supplied from the system control unit 10, and generates a spectrum shape model by Fourier-transforming the window function. FIGS. 6A and 6B show specific examples of spectrum shape models corresponding to the respective types of window shapes. Reference symbols b1 to b3 in FIG. 6B denote spectrum shape models corresponding to a rectangular window shape a1, Hanning window shape a2, and Hamming window shape shown in FIG. 6A.

The threshold setting unit 53 sets a plurality of thresholds for generating desired trace waveform data on the basis of the Doppler sensitivity Ds supplied from the Doppler sensitivity measuring unit 51, the spectrum shape model supplied from the spectrum shape model generating unit 52, and the threshold range information and threshold count information supplied from the system control unit 10.

The principle of a threshold setting method in this case will be described with reference to the graphs of FIGS. 7A and 7B. Referring to each of FIGS. 7A and 7B, the abscissa corresponds frequency; and the ordinate, power. FIG. 7A shows a spectrum shape model MD generated by the spectrum shape model generating unit 52 on the basis of the window function information supplied from the system control unit 10, and a relative noise level Nr set on the basis of the Doppler sensitivity Ds supplied from the Doppler sensitivity measuring unit 51. FIG. 7A shows a case with Doppler sensitivities Ds1 (dB) to Ds3 (dB). In this case, relative noise levels Nr1 to Nr3 are set to be lower than the maximum value (0 dB) of the spectrum shape model by Ds1 to Ds3, respectively.

Figure 7B:
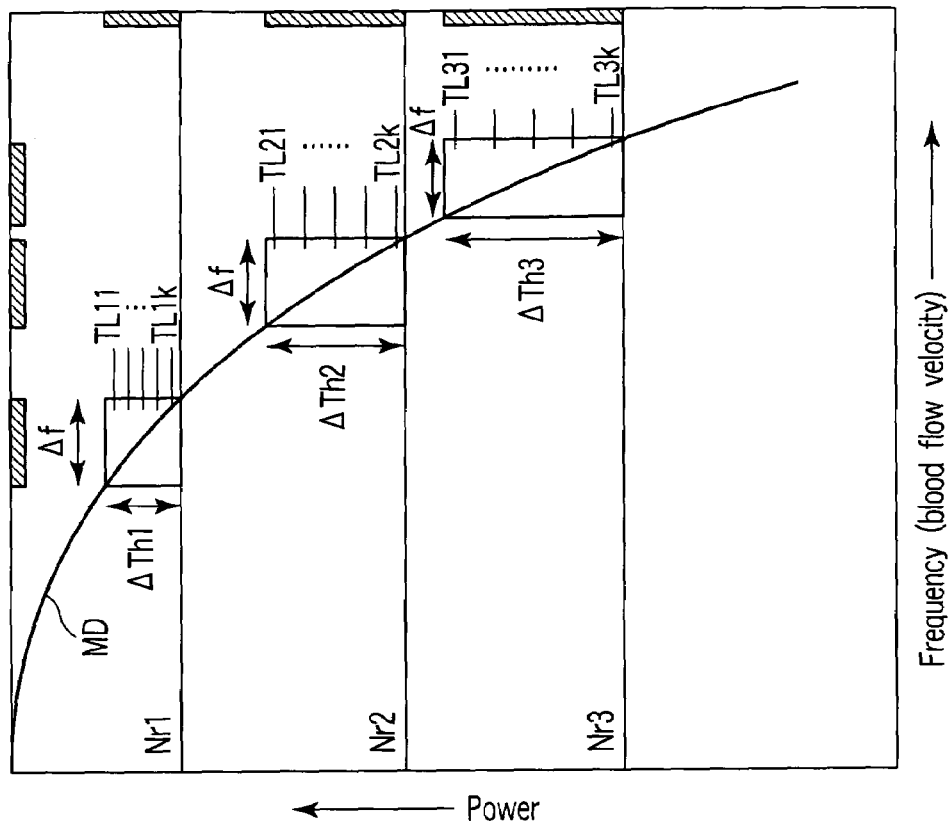
FIGS. 7A and 7B are graphs showing the principle of a threshold setting method in the first embodiment.
Figure 7A:
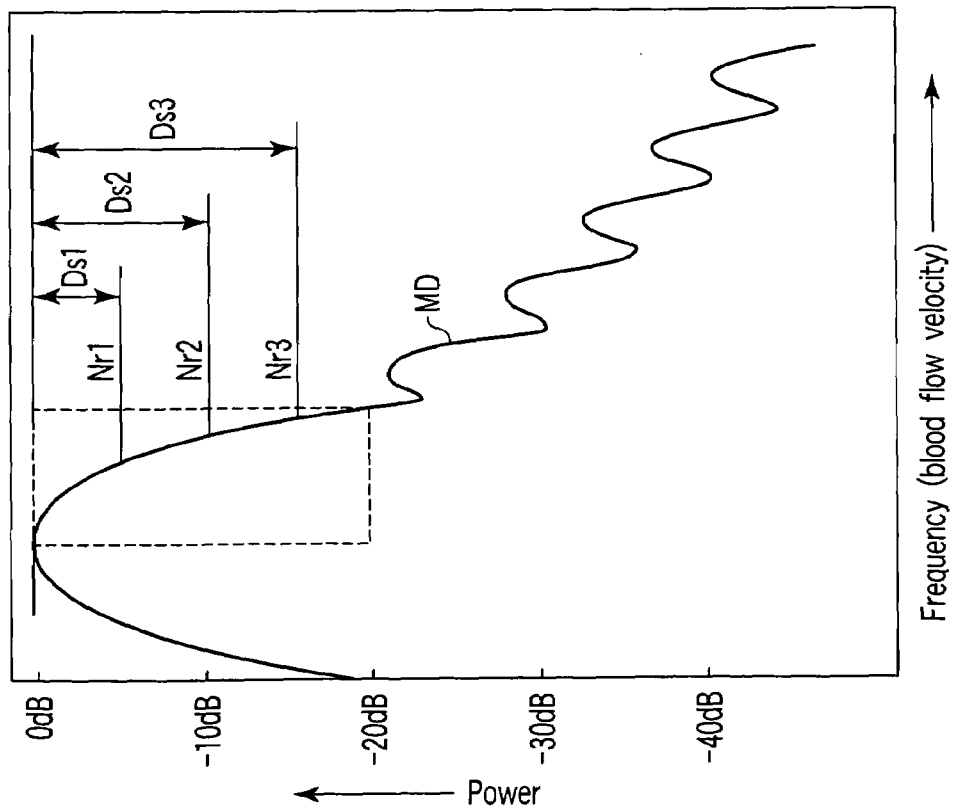

FIG. 7B is an enlarged view of the spectrum shape model MD and the relative noise levels Nr1 to Nr3 shown within the broken line frame in FIG. 7A. In this graph, threshold ranges $\Delta Th_1$ to $\Delta Th_3$ are set, which are necessary for displacements with respect to the relative noise levels Nr1 to Nr3 by a predetermined frequency displacement amount Δf. Note that the range ΔTh1 is the threshold range set with reference to the relative noise level Nr1, and the ranges ΔTh2 and ΔTh3 are the threshold ranges set with reference to the relative noise levels Nr2 and Nr3, respectively. In general, the threshold ranges ΔTh1 to ΔTh3 correspond to the magnitudes of the Doppler sensitivities Ds1 to Ds3 and have the relationship represented by ΔTh1>ΔTh2>ΔTh3.

The threshold setting unit 53 sets preset K thresholds TL1k, TL2k, and TL3k (k=1 to K) at almost equal intervals in each of the threshold ranges ΔTh1 to ΔTh3 set on the basis of the above spectrum shape model MD and relative noise levels Nr1 to Nr3. FIG. 7B shows a case wherein K=5. However, the present invention is not limited to this. Although the three relative noise levels Nr1 to Nr3 have been described above, when, for example, a relative noise level for Doppler spectrum data obtained from an object is represented by Nrx, the threshold setting unit 53 sets a threshold TLxk (k=1 to K) according to the same procedure as that described above.

Figure 8:
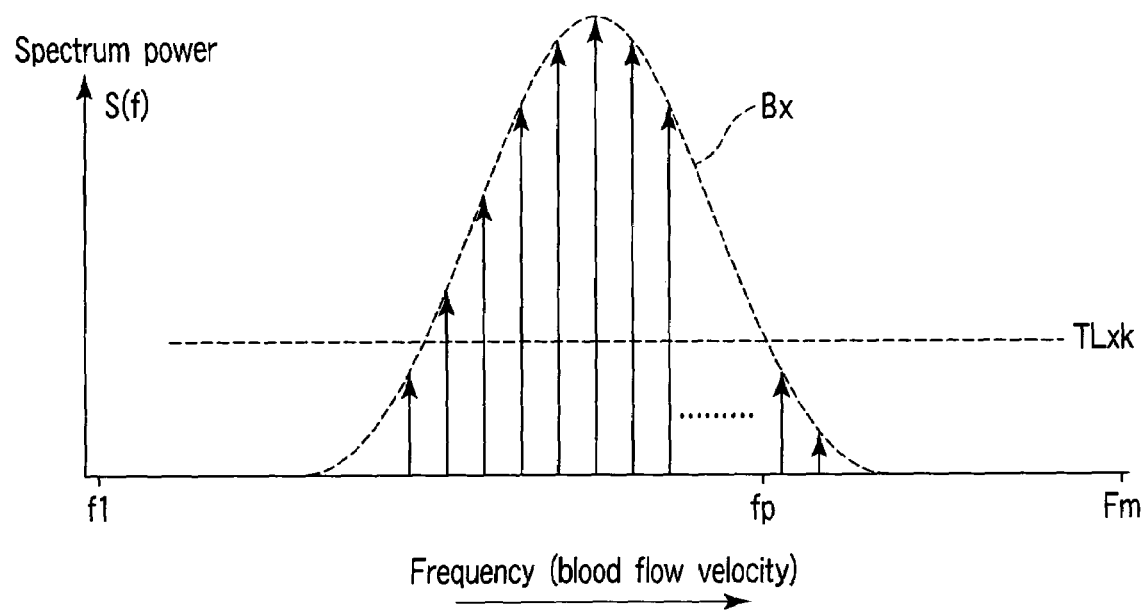
FIG. 8 is a graph showing a method of detecting the maximum frequency of Doppler spectrum data in the first embodiment.

The trace data generating unit 54 generates trace waveform data associated with the maximum blood flow velocity Vp by sequentially setting the thresholds TLxk (k=1 to K) obtained by the threshold setting unit 53 with respect to the Doppler spectrum data supplied from the spectrum data generating unit 44 of the data generating unit 4. That is, the trace data generating unit 54 detects a maximum frequency fp based on the threshold TLxk with respect to each of a plurality of Doppler spectrum data B1, B2, B3, . . . obtained by the spectrum data generating unit 44 at ΔT intervals, and generates trace waveform data indicating a temporal change in the maximum blood flow velocity Vp corresponding to the maximum frequency fp. FIG. 8 shows a method of detecting the maximum frequency fp described above, and the maximum frequency fp is detected on the basis of the intersection between the threshold TLxk set by the threshold setting unit 53 and Doppler spectrum data Bx supplied from the spectrum data generating unit 44.

The data storage unit 6 in FIG. 2A generates and stores B mode image data, color Doppler image data, and Doppler spectrum image data on the basis of the B mode data, color Doppler data, and Doppler spectrum data time-serially obtained by the data generating unit 4, and stores the trace waveform data generated by the trace waveform generating unit 5 in correspondence with the Doppler spectrum image data.

The display unit 7 comprises a display data generating circuit, conversion circuit, and monitor (not shown). The above B mode image data, color Doppler image data, Doppler spectrum image data, and trace waveform data temporarily stored in the data storage unit 6 are combined by the above display data generating circuit. The combined data is then subjected to predetermined scan conversion. The conversion circuit performs D/A conversion and TV format conversion. The resultant image is then displayed on the monitor. At this time, the Doppler spectrum image data and trace waveform data are displayed while being superimposed. For example, on the monitor of the display unit 7, an image data display area, spectrum data display area, and an accompanying information display area are set. In the image data display area, B mode image data is displayed or B mode image data and color Doppler image data are combined and displayed. In the spectrum data display area, trace waveform data superimposed on Doppler spectrum image data is displayed. In the accompanying information display area, accompanying information such as data acquisition conditions and display conditions for these data or object information is displayed.

The input unit 8 is an interactive interface comprising input devices such as a display panel on an operation panel, a trackball, a mouse, and selection buttons, is used to input patient information, set image data acquisition conditions, select an image display mode, set a frequency displacement amount Δf and threshold count K, and input various kinds of command signals such as a threshold update command signal. Note that images in the above image display mode include a B mode image, color Doppler image, and Doppler spectrum image. In addition, the image display mode of Doppler spectrum images includes selection associated with the trace waveform data of the maximum blood flow velocity Vp.

The system control unit 10 comprises a CPU and storage circuit (not shown). The input information, setting information, and selection information input from the input unit 8 are stored in the storage circuit. The CPU systematically controls the respective units of the ultrasonic Doppler measuring apparatus 100 and the overall system on the basis of the above information input from the input unit 8.

(Sequence for Generating and Displaying Trace Waveform Data)

A sequence for generating and displaying trace waveform data in this embodiment will be described next with reference to the flowchart of FIG. 9.

A case will be described below, in which the threshold range ΔTh is set with reference to the relative noise level Nr of Doppler spectrum data with respect to the spectrum shape model generated on the basis of a window function for the generation of the Doppler spectrum data, and K thresholds TL1 to TLK are set at equal intervals in the threshold range ΔTh.

Prior to the transmission/reception of ultrasonic waves with respect to an object to be examined, an operator operates the input unit 8 to input patient information, set image data generation conditions, select an image display mode, and set a window function at the time of generation of Doppler spectrum data and the frequency displacement amount Δf and threshold count K at the time of the generation of trace waveform data. The operator then stores these pieces of input information, setting information, and selection information in the storage circuit of the system control unit 10. In this embodiment, a display mode for a B mode image and Doppler spectrum image is selected as an image display mode, and a display mode for the trace waveform data of the maximum blood flow velocity Vp is further selected (step S1 in FIG. 9).

When these inputting/selecting/setting operations are complete, the operator fixes the distal end (ultrasonic wave transmission/reception surface) of the ultrasonic probe 3 at a predetermined position on the body surface of the object. Ultrasonic wave transmission/reception is then performed in the first ultrasonic wave transmission/reception direction (scanning direction θ1) to obtain B mode data and Doppler spectrum data. That is, the rate pulse generator 211 in the transmission/reception unit 2 in FIGS. 2A and 2B frequency-divides the reference signal supplied from the reference signal generating unit 1 to generate a rate pulse for determining the repetition period Tr of ultrasonic pulses applied into the object, and supplies the rate pulse to the transmission delay circuit 212.

The transmission delay circuit 212 gives the rate pulse a focusing delay time for the focusing of ultrasonic waves to a predetermined depth and a deflection delay time for the transmission of ultrasonic waves in the scanning direction θ1, and supplies the resultant rate pulse to the driving circuit 213. The driving circuit 213 then supplies driving signals generated by the rate pulse to the N ultrasonic transducers of the ultrasonic probe 3 through a cable (not shown) to apply ultrasonic pulses in the scanning direction θ1 of the object.

The ultrasonic pulses applied to the object are partially reflected by the boundary surfaces between organs having different acoustic impedances or tissues in the organs. When such ultrasonic waves are reflected by a moving reflector such as the cardiac wall and blood cells, the ultrasonic frequency is Doppler-shifted.

The reflected ultrasonic waves (reception ultrasonic waves) from tissue or blood cells in the object are received by the ultrasonic transducers of the ultrasonic probe 3 to be converted into electrical signals (reception signals). The reception signals are converted into digital signals by the independent N-channel A/D converter 221 in the reception unit 22. The reception delay circuit 222 gives the reception signals converted into the digital signals predetermined delay times. The resultant signals are added/combined by the adder 223. The resultant signal is then supplied to the B mode data generating unit 41 of the data generating unit 4.

At this time, in the reception delay circuit 222, a delay time for the focusing of reflected ultrasonic waves from a predetermined depth and a delay time for the acquisition of strong reception directivity in the scanning direction θ1 with respect to reflected ultrasonic waves are set in accordance with control signals from the system control unit 10.

The output signal from the adder 223 which is supplied to the B mode data generating unit 41 is subjected to envelope detection and logarithmic conversion. The resultant signal is then stored in the B mode image data storage area in the data storage unit 6 in FIG. 2A.

The system control unit 10 performs ultrasonic wave transmission/reception in scanning directions θ2 to θP according to the same sequence. The B mode data obtained at this time are stored in the B mode image data storage area in the data storage unit 6. That is, the B mode data corresponding to the scanning directions θ1 to θP are sequentially stored in the B mode image data storage area in the data storage unit 6 to generate B mode image data corresponding to one frame.

The display data generating circuit of the display unit 7 performs scan conversion of the 1-frame B mode image data stored in the data storage unit 6 according to a predetermined display format. The conversion circuit performs D/A conversion and TV format conversion of the image data after the scan conversion, thereby displaying the resultant image on the monitor. Subsequently, ultrasonic wave transmission/reception is repeated in the directions θ1 to θP in the same manner as described above, and the resultant B mode image data are displayed on the display unit 7 in real time.

The operator then uses an input device of the input unit 8 to set a Doppler marker in a direction θD with respect to the B mode image data of the object displayed on the monitor of the display unit 7. The range gate is moved to the position of the distance Lg on this Doppler maker to set a measurement region for the Doppler spectrum data (step S2 in FIG. 9).

At this time, B mode ultrasonic wave transmission/reception at a repetition period 2Tr in the scanning directions θ1 to θP and ultrasonic wave transmission/reception for the acquisition of Doppler spectrum data at the repetition period 2Tr in the scanning direction θD are alternately performed, and the reception signal output from the adder 223 is supplied to the Doppler signal detecting unit 42.

The Doppler signal detecting unit 42 performs quadrature phase detection of the supplied reception signal by using the mixers 422-1 and 422-2 and the LPFs 423-1 and 423-2 to detect a 2-channel Doppler signal (complex signal), and supplies the signal to the SH 441 of the spectrum data generating unit 44. The SH 441 samples/holds Doppler signals from a range gate position Lg supplied from the system control unit 10 for a predetermined period of time (e.g., 2Tr) on the basis of sampling pulses at the range gate position Lg.

In addition, the Doppler signals at the range gate position which are time-serially obtained from the SH 441 by ultrasonic wave transmission/reception performed in the scanning direction θD at the repetition period 2Tr are smoothed by the LPF 442. For the smoothed signals, the window function setting unit 443 sets a data length for the generation of Doppler spectrum data and performs weighting processing for the data. The resultant data are then stored in the storage circuit (not shown) of the FFT analyzer 444.

The computing circuit (not shown) of the FFT analyzer 444 generates Doppler spectrum data by performing FFT analysis of the Doppler signal of the predetermined data length set by the window function setting unit 443. That is, the computing circuit of the FFT analyzer 444 generates Doppler spectrum data B1 corresponding to frequencies f1 to fm by performing FFT analysis using the Doppler signals after weighing processing which are discretely supplied with a data length m (see FIGS. 4A to 4C). The generated Doppler spectrum data B1 are stored in the spectrum data storage area of the data storage unit 6 and also stored in a storage circuit (not shown) in the Doppler sensitivity measuring unit 51 of the trace waveform generating unit 5.

In the same manner, the FFT analyzer 444 of the spectrum data generating unit 44 time-serially generates Doppler spectrum data B2, B3, B4, . . . with respect to Doppler signals after weighting processing which are supplied after ΔT, 2ΔT, 3ΔT, . . . . The Doppler spectrum data are then stored in the spectrum data storage area of the data storage unit 6 to generate Doppler spectrum image data, and the generated data are stored in the storage circuit of the Doppler sensitivity measuring unit 51 (step S3 in FIG. 9).

Figure 9:
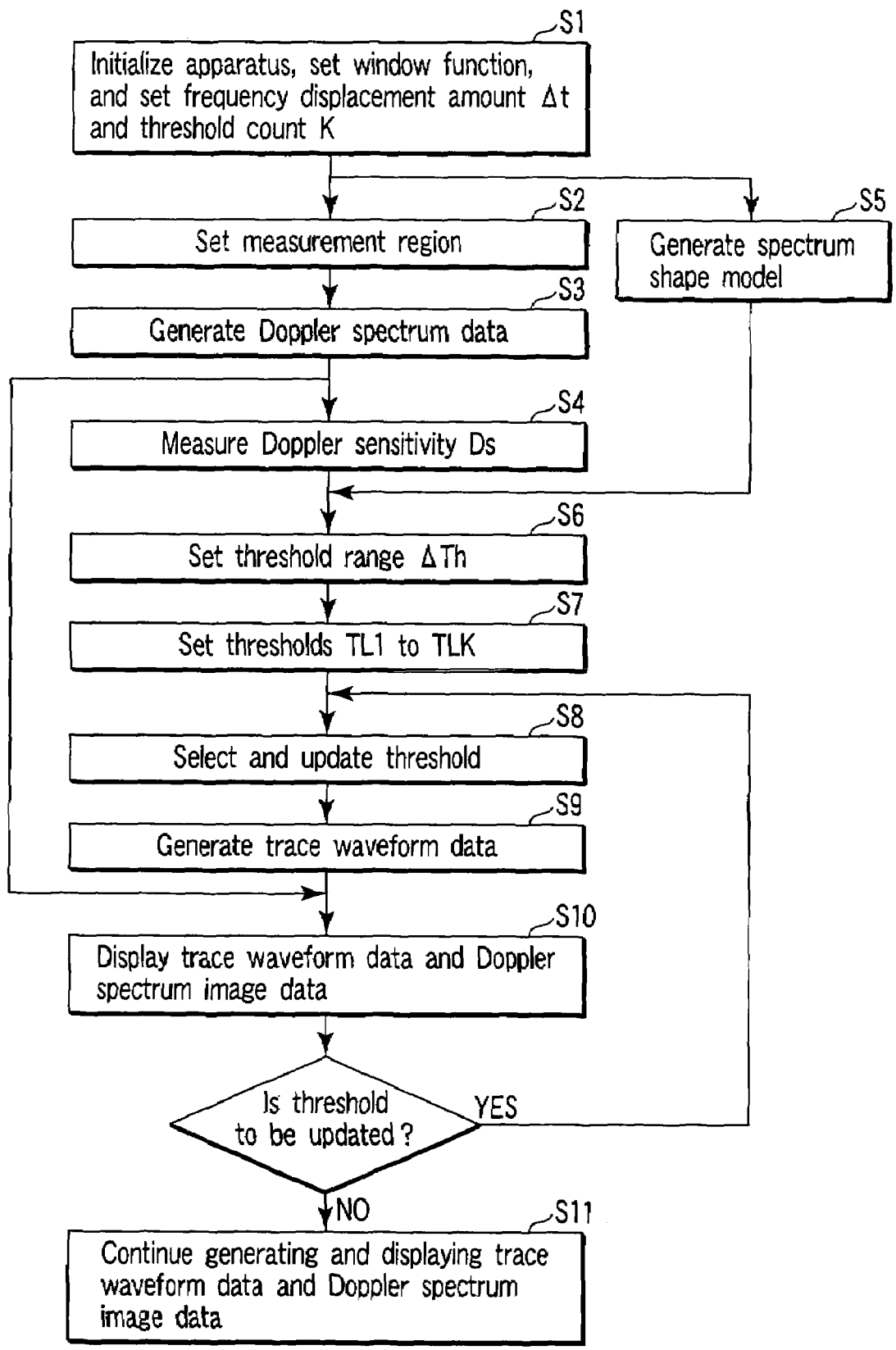
FIG. 9 is a flowchart showing a sequence for generating and displaying trace waveform data in the first embodiment.

The computing circuit of the Doppler sensitivity measuring unit 51 reads out a plurality of Doppler spectrum data stored in the storage circuit, measures the average signal level Sa and average noise level Na, and measures the Doppler sensitivity Ds on the basis of the obtained average signal level Sa and average noise level Na (step S4 in FIG. 9).

The spectrum shape model generating unit 52 of the trace waveform generating unit 5 receives window function information for the generation of Doppler spectrum data which is supplied from the system control unit 10, and generates the spectrum shape model MD by Fourier-transforming the window function (step S5 in FIG. 9).

The threshold setting unit 53 sets the threshold range ΔTh on the basis of the Doppler sensitivity Ds supplied from the Doppler sensitivity measuring unit 51, the spectrum shape model MD supplied from the spectrum shape model generating unit 52, and frequency displacement amount Δf supplied from the system control unit 10 (step S6 in FIG. 9), and also sets K thresholds TL1 to TLK at almost equal intervals in the threshold range ΔTh on the basis of the threshold count K supplied from the system control unit 10 (step S7 in FIG. 9).

When the thresholds TL1 to TLK are set, the trace data generating unit 54 automatically selects, for example, the threshold TL1 nearest to the average noise level from the thresholds TL1 to TLK supplied from the threshold setting unit 53 (step S8 in FIG. 9). The trace data generating unit 54 then detects the maximum frequency fp by setting the threshold TL 1 for each of the Doppler spectrum data time-serially supplied from the spectrum data generating unit 44 of the data generating unit 4, and generates trace waveform data representing a temporal change in the maximum blood flow velocity Vp corresponding to the maximum frequency fp (step S9 in FIG. 9). The obtained trace waveform data is supplied to the data storage unit 6 to be stored in correspondence with the Doppler spectrum image data which has already been stored.

The display unit 7 combines the Doppler spectrum image data and trace waveform data temporarily stored in the data storage unit 6 and converts the resultant data into data in a predetermined display format. The display unit 7 also performs D/A conversion and TV format conversion and displays the resultant image on the monitor (step S10 in FIG. 9).

The operator observes the above trace waveform data displayed on the monitor of the display unit 7 in real time, together with the Doppler spectrum image data. If the operator determines that the proper trace waveform data of the maximum blood flow velocity Vp is not displayed due to noise or the like, he/she operates the input unit 8 to input a command signal for updating the threshold. Upon receiving the above command signal through the system control unit 10, the trace data generating unit 54 updates the threshold TL1 to, for example, the threshold TL2, and sets the threshold TL2 for each of the Doppler spectrum data newly supplied from the spectrum data generating unit 44 of the data generating unit 4, thereby generating trace waveform data.

The obtained trace waveform data and the Doppler spectrum image data generated concurrently with the trace waveform data are displayed on the monitor of the display unit 7. The updating of the threshold and the generation and display of trace waveform data based on the updated threshold are repeated until desired trace waveform data is displayed (steps S8 to S10 in FIG. 9).

When desired trace waveform data is displayed, the generation of trace waveform data is continued while a threshold is fixed, and the obtained trace waveform data is displayed on the display unit 7, together with the Doppler spectrum image data (step S11 in FIG. 9). At this time, the B mode image data generated concurrently with the above Doppler spectrum image data and trace waveform data is preferably displayed on the display unit 7. The simultaneous display of the above data with the B mode image data makes it easy to check a measurement region.

In setting a threshold in the above embodiment, for example, a threshold nearest to the average noise level Na (the threshold TL1 in the above case) is automatically set, and the first trace waveform data is generated and displayed. When this trace waveform data is to be updated, the threshold TL1 is updated to the thresholds TL2, TL3, . . . in a stepwise manner every time a threshold update command signal is input from the input unit 8, and the trace waveform data generated on the basis of the updated threshold is displayed on the display unit 7, together with Doppler spectrum image data, in real time.

Note, however, that the threshold to be automatically set is not limited to the threshold nearest to the average noise level Na. For example, the median threshold of K thresholds set by the threshold setting unit 53 may be automatically set first, and the operator may instruct to increase/decrease the threshold upon observing the trace waveform data generated on the basis of the threshold.

As described above, according to this embodiment, when desired trace waveform data is to be generated on the basis of the Doppler spectrum data obtained by ultrasonic wave transmission/reception with respect to a measurement region of an object to be examined, an optimal threshold for the acquisition of desired trace waveform data can be efficiently selected by setting a threshold range on the basis of a spectrum shape model and Doppler sensitivity and sequentially updating the threshold to a plurality thresholds set at predetermined intervals in the threshold range. FIG. 11 is a correlation diagram on which expected values on the frequency axis and measured values obtained by this apparatus are plotted in the respective time phases. According to this correlation diagram, when data exist on a straight line with a slope of 45° (i.e., the ratio between the expected values and the measured values is 1), ideal envelope tracing is performed. As shown in FIG. 11, according to the results obtained by this apparatus, the ratios between the expected values and the measured values fall between 0.9 and 1.1. Therefore, according to this ultrasonic Doppler measuring apparatus, an optimal threshold for the acquisition of suitable trace waveform data can be efficiently selected.

In selecting an optimal threshold in the above embodiment, since the interval between adjacent thresholds is set to make the displacement amount of trace waveform data, i.e., the frequency displacement amount, become almost constant, a threshold for the generation of desired trace waveform data can be set accurately within a short period of time regardless of the magnitude of Doppler sensitivity.

Therefore, not only diagnosis accuracy and diagnosis efficiency can be improved but also the load on the operator can be greatly reduced.

Although an embodiment of the present invention has been described above, the present invention is not limited to the above embodiment, and the embodiment can be modified. For example, a spectrum shape model in the above embodiment is generated on the basis of a window function. However, such a model may be generated in consideration of a measurement region for trace waveform data, the age and disease name of the object, ultrasonic wave transmission/reception conditions such as a range gate width, and the like in addition to this window function.

If, for example, the range gate is narrow, Doppler signals with a single frequency are detected. If the range gate is wide, Doppler signals having frequency components in a wide band are detected. The bandwidth in this case depends on a turbulent/laminar blood flow. It is therefore preferable that the spectrum shape model generating unit 52 of the trace waveform generating unit 5 generate a spectrum shape model on the basis of a window function first, and then correct the spectrum shape model by a correction coefficient set in advance on the basis of the above conditions.

FIGS. 10A to 10C each show a specific example of a spectrum shape model corrected on the basis of a range gate width and a turbulent/laminar flow. FIG. 10A shows a spectrum shape model when a very narrow range gate is used. FIG. 10B shows a spectrum shape model when a turbulent flow is measured by using a relatively wide range gate. FIG. 10C shows a spectrum shape model when a laminar flow is measured by using a relatively wide range gate.

In the above embodiment, a spectrum shape model is generated on the basis of a window function having a Hanning window shape. However, a window function having another window shape, e.g., a rectangular window shape, Hamming window shape, or Gaussian window shape, may be used.

Although the case wherein a plurality of thresholds are set at equal intervals within the threshold range ΔTh has been described, threshold intervals may be uneven. For example, the above threshold interval may be set such that trace waveform data are displaced at almost equal intervals in the frequency axis direction.

SECOND EMBODIMENT

The second embodiment of the present invention will be described next. In this embodiment, a threshold range and a plurality of thresholds in the threshold range are adaptively set with reference to a mistrace wave occurrence rate.

Figure 12:
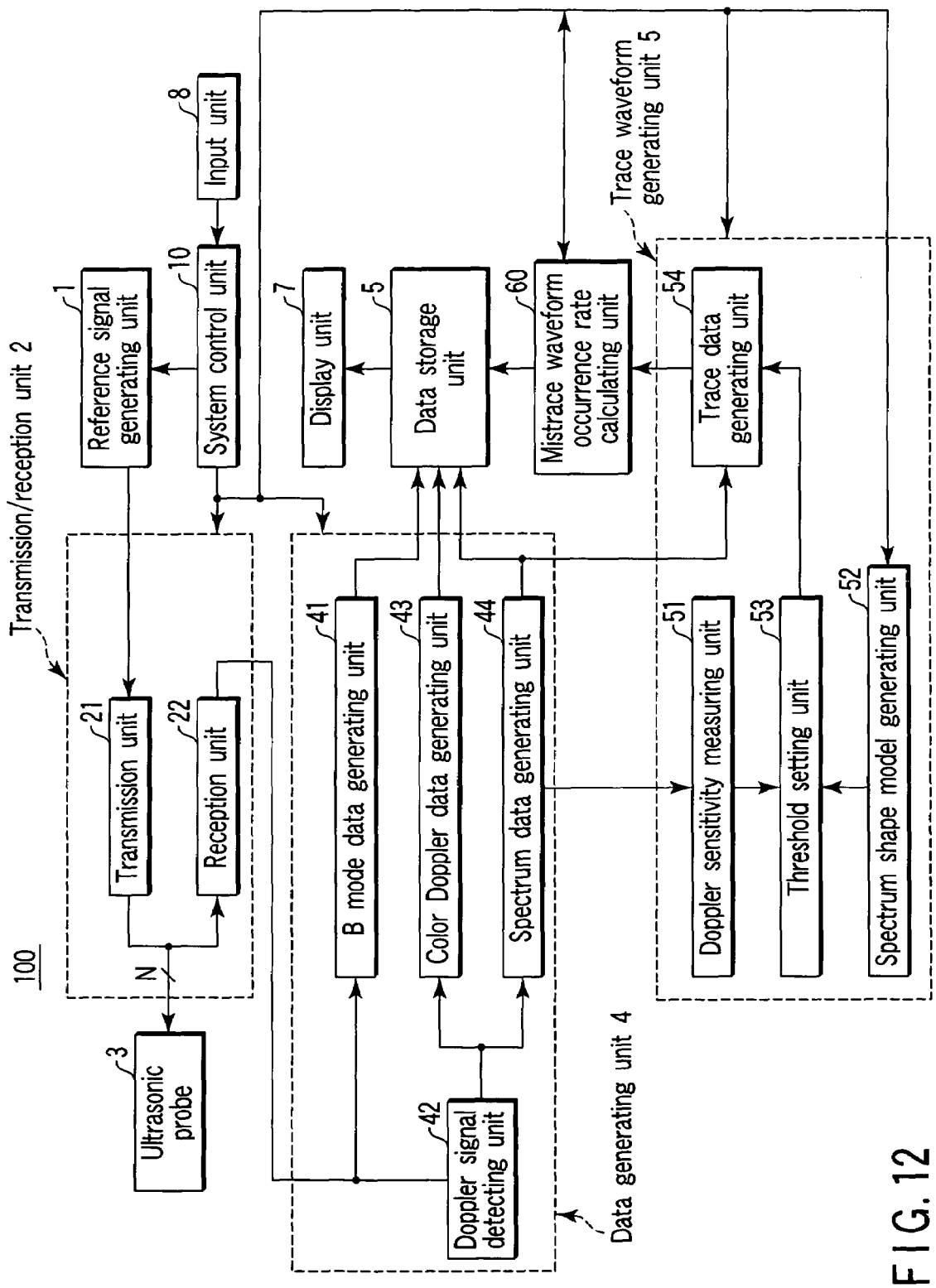
FIG. 12 is a block diagram showing an ultrasonic Doppler measuring apparatus according to the second embodiment.

FIG. 12 is a block diagram of an ultrasonic Doppler measuring apparatus according to this embodiment. This ultrasonic Doppler measuring apparatus further includes a mistrace waveform occurrence rate calculating unit 60 in addition to the arrangement shown in FIG. 2A.

A data storage unit 6 stores the image data generated by a B mode data generating unit 41, the spectrum data generated by a spectrum data generating unit 44, and the expected value data of a trace waveform for each threshold which is obtained by tracing.

Figure 13:
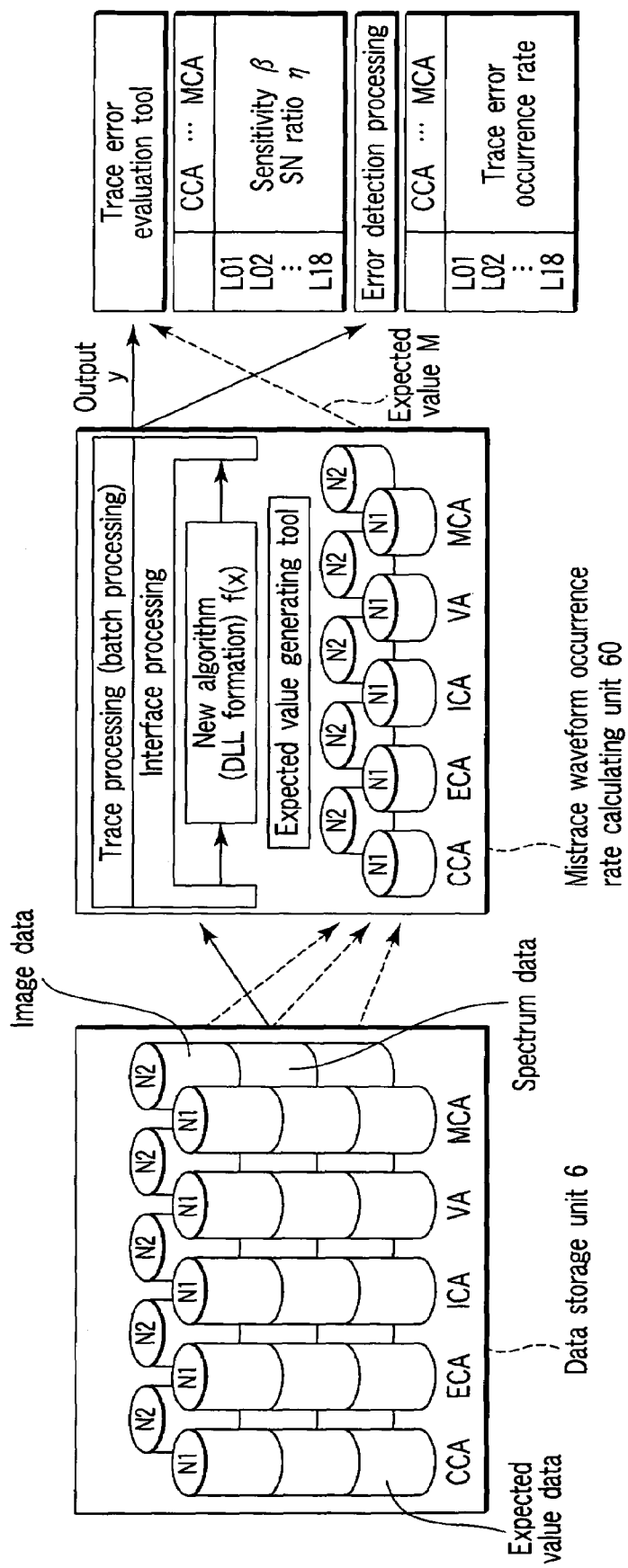
FIG. 13 is a conceptual view for explaining a method of calculating a mistrace waveform occurrence rate according to the second embodiment.

As shown in FIG. 13, the mistrace waveform occurrence rate calculating unit 60 evaluates a tracing error on the basis of the image data, spectrum data, expected value data stored in the data storage unit 6, and calculates a mistrace waveform occurrence rate for each threshold set by initialization or the like on the basis of the obtained tracing error. Note that any kind of technique can be used for this tracing error evaluation. Typically, the Taguchi method in quality engineering can be used.

A system control unit 10 calculates expected value data of a trace waveform for each threshold which is obtained by tracing. The system control unit 10 determines, on the basis of the calculated mistrace occurrence rate, whether the currently set threshold is to be changed. Upon determining that a threshold is to be set, the system control unit 10 controls threshold setting in a threshold setting unit 53 such that the mistrace occurrence rate becomes a predetermined value or less (e.g., 5% or less). This control is executed in accordance with, for example, a table stored in the data storage unit 6 such that the threshold increases when a mistrace waveform appears inside the expected value waveform of an envelope waveform displayed as a spectrum, whereas the threshold decreases when a mistrace waveform appears outside the expected value waveform.

The threshold setting unit 53 changes and sets a threshold range and a plurality of thresholds in the threshold range in accordance with an instruction from the system control unit 10 so as to make the mistrace occurrence rate become a predetermined value or less.

According to the above arrangement, when desired trace waveform data is to be generated on the basis of Doppler spectrum data obtained by ultrasonic wave transmission/reception with respect to a measurement region of an object to be examined, a threshold range is set with reference to a mistrace waveform occurrence rate, and a plurality of thresholds set at predetermined intervals within the threshold range are sequentially updated, thereby efficiently selecting an optimal threshold by which desired trace waveform data can be obtained.

The present invention is not limited to the above embodiments, and constituent elements can be modified and embodied in the execution stage within the spirit and scope of the invention.

Each of the above embodiments has exemplified the arrangement for controlling a threshold for trace waveforms in accordance with a predetermined reference to obtain an optimal trace waveform. However, the present invention is not limited to this. For example, a trace waveform can be optimized by controlling a noise level by adjusting a gain in ultrasonic scanning while fixing a threshold, and controlling an S/N ratio by adjusting a dynamic range. In addition, gain and dynamic range adjusting in ultrasonic scanning may be combined with threshold control for trace waveform described in each embodiment.

In addition, various inventions can be formed by proper combinations of a plurality of constituent elements disclosed in the above embodiments. For example, several constituent elements may be omitted from all the constituent elements disclosed in the above embodiments. Furthermore, constituent elements in the different embodiments may be properly combined.

What is claimed is:

1. An ultrasonic Doppler measuring apparatus comprising:
an ultrasonic probe having an ultrasonic transducer which performs ultrasonic wave transmission/reception in a predetermined direction of an object to be examined;
a transmission unit which transmits an ultrasonic wave by driving the ultrasonic transducer;
a reception unit which receives a reception signal from the object which is obtained by transmission/reception of the ultrasonic wave;
a Doppler signal detecting unit which detects a Doppler signal with respect to the reception signal;
a spectrum data generating unit which time-serially generates Doppler spectrum data by setting a predetermined window function for the Doppler signals at a predetermined region which are time-serially obtained by repeating ultrasonic wave transmission/reception in the predetermined direction;
a Doppler sensitivity measuring unit which measures a Doppler sensitivity on the basis of said plurality of Doppler spectrum data generated by the spectrum data generating unit;
a spectrum shape model generating unit which generates a spectrum shape model on the basis of the window function;
a threshold setting unit which sets a threshold range in which trace waveform data displaces by a predetermined amount in a frequency axis direction and sets a plurality of thresholds in the threshold range on the basis of the spectrum shape model and the Doppler sensitivity;
a trace data generating unit which generates as the trace waveform data a temporal change in Doppler frequency of the Doppler spectrum data which corresponds to a threshold selected from said plurality of thresholds; and
a display unit which displays the trace waveform data.

2. An apparatus according to claim 1, wherein the threshold setting unit sets an interval between thresholds in the threshold range such that trace waveform data generated on the basis of adjacent thresholds are arranged at substantially equal intervals in the frequency axis direction.

3. An apparatus according to claim 1, which further comprises an input unit which inputs an instruction signal to select or update a predetermined threshold from said plurality of thresholds set by the threshold setting unit, and in which the trace data generating unit generates trace waveform data on the basis of the threshold selected or updated by the input unit.

4. An apparatus according to claim 1, wherein the Doppler sensitivity measuring unit measures the Doppler sensitivity on the basis of an average signal level and an average noise level obtained from a plurality of time serially obtained Doppler spectrum data.

5. An apparatus according to claim 1, wherein the Doppler sensitivity measuring unit measures an average signal level from an average value of maximum signal components of a plurality of time serially obtained Doppler spectrum data in a time axis direction, and measures an average noise level from an average value of noise components in the frequency axis direction and time axis direction.

6. An apparatus according to claim 1, wherein the spectrum shape model generating unit generates the spectrum shape model by Fourier transforming the window function.

7. An apparatus according to claim 1, wherein the spectrum shape model generating unit comprises a model correcting unit which corrects the spectrum shape model on the basis of at least one of a measuring region for trace waveform data, an ultrasonic wave transmission/reception condition, and object information.

8. An apparatus according to claim 1, wherein the threshold setting unit sets a relative noise level for the spectrum shape model on the basis of the Doppler sensitivity, and sets the threshold range with reference to the relative noise level.

9. An apparatus according to claim 1, wherein the spectrum data generating unit generates the Doppler spectrum data by Fourier transforming a Doppler signal in a predetermined interval which has undergone weighting processing with the window function.

10. An apparatus according to claim 9, wherein the spectrum data generating unit performs weighting processing on the basis of one of a rectangular window shape, a Hanning window shape, a Hamming window shape, and a Gaussian window shape.

11. An ultrasonic Doppler measuring apparatus control method comprising:
- transmitting an ultrasonic wave by driving an ultrasonic transducer which performs ultrasonic wave transmission/reception in a predetermined direction of an object to be examined;
- receiving a reception signal from the object which is obtained by transmission/reception of the ultrasonic wave;
- detecting a Doppler signal from the reception signal;
- time serially generating Doppler spectrum data by setting a predetermined window function for the Doppler signals at a predetermined region which are time serially obtained by repeating ultrasonic wave transmission/reception in the predetermined direction;
- measuring a Doppler sensitivity on the basis of said plurality of generated Doppler spectrum data;
- generating a spectrum shape model on the basis of the window function;
- setting a threshold range in which trace waveform data displaces by a predetermined amount in a frequency axis direction and setting a plurality of thresholds in the threshold range on the basis of the spectrum shape model and the Doppler sensitivity;
- generating a temporal change in Doppler frequency of the spectrum data which corresponds to a threshold selected from said plurality of thresholds as the trace waveform data; and
- displaying the trace waveform data.

12. A method according to claim 11, wherein in setting the threshold range, an interval between thresholds is set in the threshold range such that trace waveform data generated on the basis of adjacent thresholds are arranged at substantially equal intervals in the frequency axis direction.

13. A method according to claim 11, which further comprises inputting an instruction signal to select or update a predetermined threshold from said plurality of thresholds wherein the predetermined threshold is the basis for generating the temporal change in Doppler frequency of the spectrum data.

14. A method according to claim 11, wherein in measuring the Doppler sensitivity, the Doppler sensitivity is measured on the basis of an average signal level and average noise level obtained from a plurality of time serially obtained Doppler spectrum data.

15. A method according to claim 11, wherein in measuring the Doppler sensitivity, an average signal level is measured from an average value of maximum signal components of a plurality of time serially obtained Doppler spectrum data in a time axis direction, and an average noise level is measured from an average value of noise components in the frequency axis direction and time axis direction.

16. A method according to claim 11, wherein in generating the spectrum shape model, the spectrum shape model is generated by Fourier transforming the window function.

17. A method according to claim 11, wherein in generating the spectrum shape model, the spectrum shape model is corrected on the basis of at least one of a measuring region for trace waveform data, an ultrasonic wave transmission/reception condition, and object information.

18. A method according to claim 11, wherein in setting the threshold range, a relative noise level for the spectrum shape model is set on the basis of the Doppler sensitivity, and the threshold range is set with reference to the relative noise level.

19. A method according to claim 11, wherein in generating the spectrum data, the Doppler spectrum data is generated by Fourier transforming a Doppler signal in a predetermined interval which has undergone weighting processing with the window function.

20. A method according to claim 19, wherein weighting processing is performed on the basis of one of a rectangular window shape, a Hanning window shape, a Hamming window shape, and a Gaussian window shape.

* * * * *